(12) United States Patent
Choi et al.

(10) Patent No.: US 9,861,548 B2
(45) Date of Patent: Jan. 9, 2018

(54) METHOD AND SYSTEM FOR CONVERTING AND RECONSTRUCTING SIGNAL, METHOD AND APPARATUS FOR CONVERTING ORIGINAL SIGNAL, AND METHOD FOR RECONSTRUCTING ORIGINAL SIGNAL

(71) Applicant: Samsung Electronics Co., Ltd., Suwon-Si, Gyeonggi-Do (KR)

(72) Inventors: Byung Kwon Choi, Suwon-si (KR); Kee Hong Seo, Seoul (KR); Young Do Kwon, Yongin-si (KR); Tae Sin Ha, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 154 days.

(21) Appl. No.: 14/499,621

(22) Filed: Sep. 29, 2014

(65) Prior Publication Data

US 2015/0157525 A1    Jun. 11, 2015

(30) Foreign Application Priority Data

Dec. 6, 2013 (KR) .................. 10-2013-0151436

(51) Int. Cl.
| | | |
|---|---|---|
| *G06F 19/00* | (2011.01) | |
| *A61H 1/02* | (2006.01) | |
| *A61H 3/00* | (2006.01) | |
| *G06K 9/00* | (2006.01) | |

(Continued)

(52) U.S. Cl.
CPC .............. *A61H 1/024* (2013.01); *A61B 5/112* (2013.01); *A61B 5/7232* (2013.01); *A61H 1/0244* (2013.01); *A61H 3/00* (2013.01); *G06K 9/00342* (2013.01); *G06K 9/00543* (2013.01); *A61B 5/002* (2013.01); *A61B 5/0022* (2013.01); *A61B 5/1114* (2013.01); *A61B 5/7475* (2013.01);

(Continued)

(58) Field of Classification Search
CPC ..... H04N 2201/04712; G06K 9/00523; G06K 2207/1018; G06K 7/10732; G06K 7/10752; G06K 9/2009; G06K 7/10594; G06K 9/26; G06K 9/325; G06K 9/00342; G06K 9/00543; H03H 17/0201; G06T 5/003
USPC ............................ 700/245; 601/23; 600/587
See application file for complete search history.

(56) References Cited

U.S. PATENT DOCUMENTS 8,585,620 B2 * 11/2013 McBean ............... A61F 5/0127
                                                                      600/546
2002/0107649 A1    8/2002 Takiguchl et al.

(Continued)

FOREIGN PATENT DOCUMENTS

| | | | |
|---|---|---|---|
| JP | 2004147793 A | 5/2004 | |
| JP | 2008154733 A | 7/2008 | |
| JP | 2009207789 A | 9/2009 | |

*Primary Examiner* — Ronnie Mancho
(74) *Attorney, Agent, or Firm* — Harness, Dickey & Pierce, P.L.C.

(57) ABSTRACT

Disclosed herein is a method of converting and reconstructing a signal, including: at a data generator, acquiring signal-analyzed data from an original signal, wherein the signal-analyzed data includes at least one feature point acquired from the original signal; transmitting and receiving the signal-analyzed data and at least one reference data corresponding to the signal-analyzed data; and reconstructing the original signal based on the signal-analyzed data and the at least one reference data to acquire a reconstructed signal.

17 Claims, 27 Drawing Sheets

(51) Int. Cl.
*A61B 5/00* (2006.01)
*A61B 5/11* (2006.01)

(52) U.S. Cl.
CPC ....... *A61B 2505/07* (2013.01); *A61B 2505/09* (2013.01); *A61H 2201/1215* (2013.01); *A61H 2201/165* (2013.01); *A61H 2201/1676* (2013.01); *A61H 2201/501* (2013.01); *A61H 2201/5007* (2013.01); *A61H 2201/5046* (2013.01); *A61H 2201/5061* (2013.01); *A61H 2201/5064* (2013.01); *A61H 2201/5069* (2013.01); *A61H 2201/5084* (2013.01); *A61H 2201/5092* (2013.01); *A61H 2201/5097* (2013.01); *G05B 2219/40305* (2013.01)

(56) References Cited

U.S. PATENT DOCUMENTS

| | | | |
|---|---|---|---|
| 2003/0009259 A1* | 1/2003 | Hattori | B62D 57/032 700/245 |
| 2006/0200034 A1* | 9/2006 | Ricci | G06K 9/00523 600/513 |
| 2010/0121232 A1* | 5/2010 | Sankai | A61H 3/008 601/23 |
| 2010/0152600 A1* | 6/2010 | Droitcour | A61B 5/05 600/534 |
| 2012/0113287 A1* | 5/2012 | Johnson | H04N 5/217 348/222.1 |
| 2013/0165820 A1 | 6/2013 | Lin et al. | |
| 2013/0330162 A1* | 12/2013 | Horinouchi | B25J 5/007 414/730 |
| 2014/0212243 A1* | 7/2014 | Yagi | A61H 3/00 414/2 |
| 2014/0276304 A1* | 9/2014 | Dollar | A61F 5/0102 602/16 |
| 2015/0073721 A1* | 3/2015 | Briggs | A61B 5/7246 702/19 |
| 2015/0088043 A1* | 3/2015 | Goldfield | A61F 5/01 602/6 |
| 2015/0134079 A1* | 5/2015 | Yoon | A61F 2/68 623/27 |
| 2015/0157525 A1* | 6/2015 | Choi | A61B 5/7232 700/245 |
| 2015/0231018 A1* | 8/2015 | Shim | A61H 3/00 623/24 |

* cited by examiner

METHOD AND SYSTEM FOR CONVERTING AND RECONSTRUCTING SIGNAL, METHOD AND APPARATUS FOR CONVERTING ORIGINAL SIGNAL, AND METHOD FOR RECONSTRUCTING ORIGINAL SIGNAL

CROSS-REFERENCE TO RELATED APPLICATION

This application claims the benefit of Korean Patent Application No. 2013-0151436, filed on Dec. 6, 2013 in the Korean Intellectual Property Office, the entire disclosure of which is incorporated herein by reference.

BACKGROUND

1. Field

Example embodiments relate to a method, an apparatus and/or a system for converting and reconstructing a signal.

2. Description of the Related Art

A wearable apparatus may be worn on a human or an animal to perform various functions, such as assisting the human's or animal's motions or collecting various kinds of information about the human's or animal's motions. Examples of the wearable apparatus include a walking assistance apparatus for assisting a human's walking, a watch, and a wearable camera.

A walking assistance robot is a wearable apparatus for assisting a user's walking by applying a force to the user's muscles to assist the user with walking. The walking assistance robot may be secured on a wearer's hips, femoral regions, or shins. The walking assistance robot may apply a desired (or, alternatively, a predetermined) force, for example, torque to the wearer's muscle or joint through mechanical means such as an actuator to assist motions of the muscle or joint, thereby helping the wearer's walking.

SUMMARY

Example embodiments provide a method and/or system for converting and reconstructing a signal, a method and apparatus for converting an original signal, and a method and apparatus for reconstructing an original signal, capable of converting an original signal into a relatively small size of data and properly reconstructing the original signal based on the converted data.

Additional aspects of the example embodiments will be set forth in part in the description of some of the example embodiments which follows and, in part, will be obvious from the description, or may be learned by practice of the example embodiments.

Some example embodiments relate to a method of converting and reconstructing a signal.

In some example embodiments, the method of converting and reconstructing a signal includes: at a data generator, acquiring signal-analyzed data from an original signal, wherein the signal-analyzed data includes at least one feature point acquired from the original signal; transmitting and receiving the signal-analyzed data and at least one reference data corresponding to the signal-analyzed data; and reconstructing the original signal based on the signal-analyzed data and the at least one reference data to acquire a reconstructed signal.

Some example embodiments relate to a system of converting and reconstructing a signal.

In some example embodiments the system includes: a data generator configured to acquire signal-analyzed data including at least one feature point acquired from a signal pattern of an original signal, from the original signal, and to transmit the signal-analyzed data and at least one reference data corresponding to the original signal; and a reconstructing unit configured to receive the signal-analyzed data and the at least one reference data, and to reconstruct the original signal based on the signal-analyzed data and the at least one reference data, thereby acquiring a reconstructed signal.

Some example embodiments relate to a method of converting an original signal.

In some example embodiments, the method of converting an original signal includes: acquiring an original signal; deciding at least one reference data corresponding to the original signal; acquiring signal-analyzed data from the original signal, wherein the signal-analyzed data includes at least one feature point acquired from a signal pattern of the original signal; and storing the signal-analyzed data and at least one reference data corresponding to the original signal.

Some example embodiments relate to a signal converting apparatus.

In some example embodiments, the signal converting apparatus includes: a signal output unit configured to output one or more original signals; a storage unit configured to store at least one reference data corresponding to at least one original signal of the one or more outputted original signals; and a signal analysis unit configured to acquire signal-analyzed data from the original signal, to decide at least one reference data corresponding to the one or more outputted original signals, and to store the signal-analyzed data and the at least one reference data in the storage unit.

Some example embodiments relate to a method of reconstructing an original signal.

In some example embodiments, the method of reconstructing an original signal includes: acquiring signal-analyzed data including at least one feature point extracted from an original signal, and at least one reference data corresponding to the original signal; acquiring a point of the reference data, corresponding to the feature point, from the reference data, and partitioning the reference data based on the point; and modifying the partitioned reference data, and combining the modified, partitioned reference data to acquire a reconstructed signal.

According to some example embodiments, an original signal may be converted into a small size of data, and properly reconstructed based on the converted data.

According to the method, system, and apparatus of some example embodiments as described above, since an original signal can be converted into a small size of data, even a large amount of original data may be stored in a small capacity of storage space. Accordingly, a large capacity of storage space may not be necessary.

Also, according to the method, system, and apparatus as described above, since an original signal can be converted into a small size of data so that a large amount of data can be transmitted with low power, application of lower power to a communication module is allowed.

If the method, system, and apparatus described above are applied to a walking assistance apparatus, an amount of walking data of the walking assistance apparatus may be reduced so that a storage unit having a smaller capacity of storage space can be used. Also, since an amount of transmission data can be reduced, a transmission time and consumption power required for transmission can be reduced. Furthermore, since a relatively small size of a power supply unit can be used in the walking assistance apparatus, it is possible to reduce the volume or weight of the walking assistance apparatus. As a result, a user can more conveniently utilize the walking assistance apparatus.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
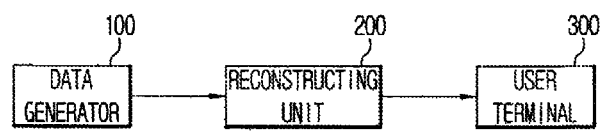
FIG. 1 is a conceptual diagram of a system for transmitting and reconstructing data, according to some example embodiments.

Reference will now be made in detail to example embodiments, some examples of which are illustrated in the accompanying drawings, wherein like reference numerals refer to like elements throughout.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Hereinafter, a system of converting and reconstructing a signal, according to some example embodiment, will be described with reference to FIGS. 1 to 20.

FIG. 1 is a conceptual diagram of a system for transmitting and reconstructing data, according to some example embodiments.

Referring to FIG. 1, a system for transmitting and reconstructing data may include a data generator 100 and a reconstructing unit 200. The data generator 100 may connect to the reconstructing unit 200 through a wired/wireless communication network to transmit or receive data to or from the reconstructing unit 200. The data generator 100 may transmit or receive data to and/or from the reconstructing unit 200 through both a wired communication network and a wireless communication network.

The wired communication network may be a communication network capable of transmitting and receiving electrical signals using communication medium such as wires. The communication medium for the wired communication network may include a loaded cable, a coaxial cable, and an optical fiber cable. The wireless communication network means a communication network capable of transmitting and receiving electrical signals using electric waves without using medium such as a cable. The wireless communication network may be established using one of various wireless communication methods. The wireless communication network may be a short-range or long-range wireless communication network. The wireless communication network may transmit data wirelessly using, for example, Bluetooth communication (Blooth™), Zigbee communication (Zigbee™), WirelessHART communication, Near Field Communication (NFC), Wireless Fidelity (Wi-Fi) communication, Wi-Fi Direct communication, Global System for Mobile Communications (GSM)/3rd Generation Partnership Project (3GPP)-based communication (GSM, High-Speed Downlink Packet Access (HSDPA), Long Term Evolution (LTE) Advanced, etc.), 3GPP2-based communication (Code Division Multiple Access (CDMA), etc.), or Worldwide Interoperability for Microwave Access (WiMAX)-based communication (Wireless Broadband (Wibro), etc.).

The data generator 100 may acquire transmission data from an original signal, and transmit the transmission data to the reconstructing unit 200. The transmission data may include signal-analyzed data acquired from the original signal, and reference data corresponding to the signal-analyzed data. The data generator 100 may acquire the transmission data by packetizing the signal-analyzed data and the reference data.

According to some example embodiments, the data generator 100 may be included in a walking assistance robot or a vehicle. Also, the data generator 100 may be included in at least one among a server computer, a desktop computer, a laptop computer, a smart phone, a cellular phone, a tablet PC, a personal digital assistant (PDA), and a navigation system. Also, the data generator 100 may be included in various apparatuses capable of sensing or measuring a motion of an object to acquire a signal regarding the motion of the object.

Figure 2:
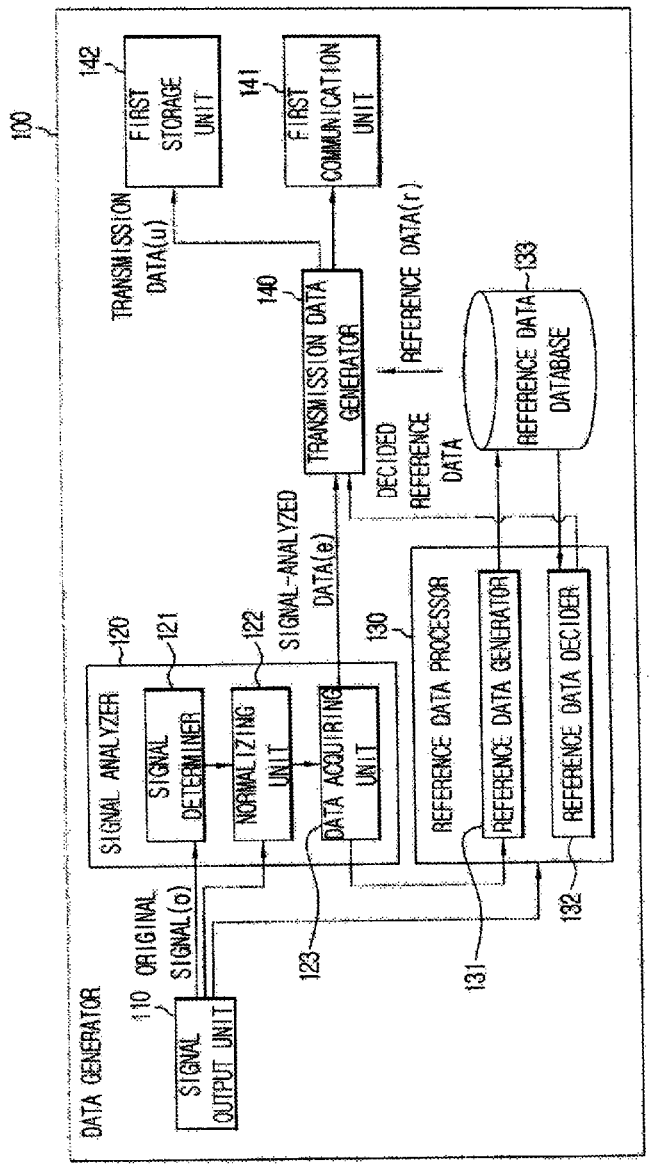
FIG. 2 is a block diagram of a data generator according to some example embodiments.

FIG. 2 is a block diagram of the data generator 100 according to some example embodiments.

Referring to FIG. 2, the data generator 100 may include a signal output unit 110, a signal analyzer 120, a reference data processor 130, a transmission data generator 140, a first communication unit 141, and a first storage unit 142. The data generator 100 may include all or a part of the above-mentioned components.

The signal output unit 110 may output an original signal "o" to at least one of the signal analyzer 120 and the reference data processor 130. According to some example embodiments, the signal output unit 110 may generate the original signal o corresponding to an external condition. More specifically, the signal output unit 110 may generate and output the original signal o according to a change of an external condition applied to the signal output unit 110 or to another medium connected to the signal output unit 110.

For example, the signal output unit 110 may sense or measure various gestures, such as a human's or animal's walking gesture or breathing gesture, or changes of such gestures, and output the original signal o corresponding to the results of the sensing or measurement. For example, the signal output unit 110 may be an optical sensor, a motion sensor, a gravity sensor, or an accelerometer. The signal output unit 110 may be an encoder installed in a prime mover or the like. Also, the signal output unit 110 may be one of various kinds of apparatuses or means capable of sensing an external stimulus and outputting an electrical signal corresponding to the sensed external stimulus.

According to other example embodiments, the original signal o may be stored in advance and the signal output unit 110 may output the stored original signal o. In this case, the original signal o previously acquired and stored in the signal output unit 110 may be a signal acquired by sensing or measuring various gestures or changes in such gestures, as described above.

According to still other example embodiments, the signal output unit 110 may be a device for generating a desired (or, alternatively, a predetermined) signal according to a user's manipulation. In this case, the signal generated according to the user's manipulation may be the original signal o. The device for generating the signal according to the user's manipulation may be an input unit. The input unit may be at least one among various physical buttons, a keyboard, a keypad, a mouse, a track-ball, a wheel input unit, and a touch screen.

The original signal o output from the signal output unit 110 may be an electrical signal processed such that it can be processed by a computer. The electrical signal may be a digital signal or an analog signal. The original signal o may be expressed as a waveform.

Figure 3:
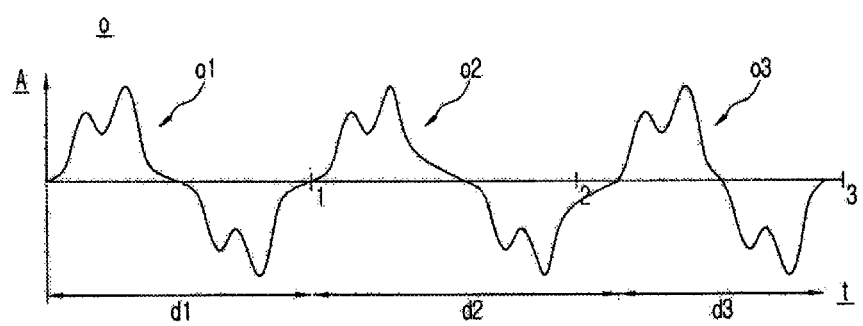
FIG. 3 is a graph showing an example of an original signal.

FIG. 3 is a graph showing an example of an original signal o expressed as a waveform. In FIG. 3, the x-axis represents time, and the y-axis represents amplitude. In the graph showing the waves of the original signal o, the time represented on the x-axis is denoted by t, and the amplitude represented on the y-axis is denoted by A.

As shown in FIG. 3, the original signal o may be a pulse signal having a desired (or, alternatively, a predetermined) pattern. The original signal o may be divided into a plurality of periods including a first period d1, a second period d2, and a third period d3. The first, second, and third periods d1, d2, and d3 may have the same time length. For example, the first, second, and third periods d1, d2, and d3 may have the same time length of 0.001 seconds (1000 hz in frequency). However, the first, second, and third periods d1, d2, and d3 may have different time lengths, respectively, as shown in FIG. 3. For example, the first period d1 may have a time length of 0.0014 seconds, the second period d2 may have a time length of 0.0016 seconds, and the third period d3 may have a time length of 0.001 seconds. However, the above-mentioned periods of the first, second, and third periods d1, d2, and d3 are only examples, and the periods of the first, second, and third periods d1, d2, and d3 may vary depending on various factors, such as the type or characteristics of the signal or the output time of the signal. First, second, third original signals o1, o2, and o3 of the respective first, second, and third periods d1, d2, and d3 may have the same waveform. In other words, the waveforms of first, second, and third original signals o1, o2, and o3 may be the same for the respective first, second, and third periods d1, d2, and d3. However, the original signals o1, o2, and o3 of the periods d1, d2, and d3 may have different waveforms. That is, the waveforms of the first, second, and third original signals o1, o2, and o3 may change depending on the respective first, second, third periods d1, d2, and d3. In this case, the waveforms of the original signals o1, o2, and o3 may change according to a predetermined pattern. Also, the original signals o1, o2, and o2 for the respective periods d1, d2, and d3 may have the same amplitude or different amplitudes. For example, as shown in FIG. 3, the maximum amplitude of the second original signal o2 corresponding to the second period d2 may be greater than the maximum amplitude of the third original signal o3 corresponding to the third period d3.

Referring again to FIG. 2, the original signal o output from the signal output unit 110 may be transferred only to the signal analyzer 120, or only to the reference data processor 130. Also, the original signal o may be transmitted to both the signal analyzer 120 and the reference data processor 130 as necessary. According to some example embodiments, the original signal o output from the signal output unit 110 may be converted into a digital signal or an analog signal by an analog/digital converter (not shown), and then transferred to at least one of the signal analyzer 120 and the reference data processor 130. Also, the original signal o may be amplified by an amplifier, and then transferred to at least one of the signal analyzer 120 and the reference data processor 130.

The signal analyzer 120 may receive the original signal o, and analyze the original signal o to acquire signal-analyzed data "e". The signal analyzer 120 may include a signal determiner 121, a normalizing unit 122, and a data acquiring unit 123.

The signal determiner 121 may determine whether or not the original signal o is a signal for acquiring signal-analyzed data e. The signal-analyzed data e may include at least one feature point acquired from the original signal o. For example, the signal determiner 121 may determine whether the amplitude of the original signal o is in a desired (or, alternatively, a predetermined) amplitude range or whether the period of the original signal o is in a desired (or, alternatively, a predetermined) period range, and determine whether to acquire signal-analyzed data e from the original signal o according to the result of the determination. Also, the signal determiner 121 may determine whether the original signal o has a desired (or, alternatively, a predetermined) pattern of waveform, and determine whether to acquire signal-analyzed data e from the original signal o, according to the result of the determination.

The normalizing unit 122 may normalize the original signal o to acquire a normalized original signal Onormal. Normalization may include modifying the original signal o according to a desired (or, alternatively, a predetermined) rule such that the original signal o can be easily used. The normalizing unit 122 may normalize the original signal o by modifying the period (frequency) or amplitude of the original signal o.

Figure 4:
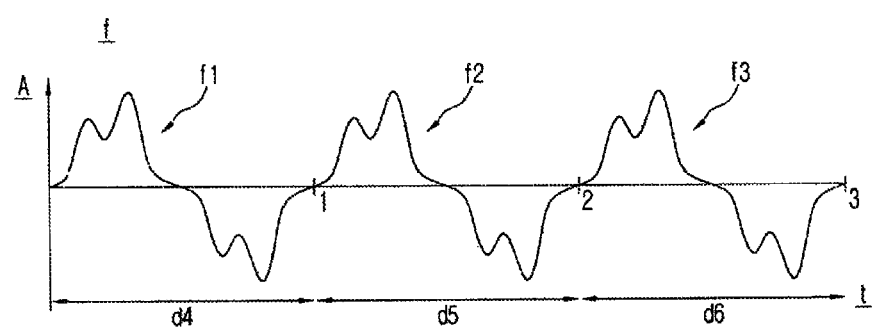
FIG. 4 is a graph showing an example of a normalized original signal.

FIG. 4 is a graph showing an example of a normalized original signal.

Referring to FIGS. 3 and 4, the original signals o1, o2, and o3 may have different periods d1, d2, and d3. The normalizing unit 122 may acquire new original signals f1, f2, and f3 of new periods d4, d5, and d6 by modifying the periods d1, d2, and d3 of the original signals o1, o2, and o3, wherein the new periods d4, d5, and d6 of the new original signals f1, f2, and f3 may have the same time length. As such, the normalizing unit 122 may acquire a normalized original signal Onormal having a constant period by equalizing the different periods d1, d2, and d3. The period of the normalized original signal Onormal may be decided in consideration of easiness of computation. For example, the period of the normalized original signal Onormal may be 0.001 seconds. As another example, the period of the normalized original signal Onormal may be the same as the period of reference data r.

The data acquiring unit 123 may acquire signal-analyzed data e from the original signal o output from the signal output unit 110, or from the original signal Onormal normalized by the normalizing unit 122. The signal-analyzed data e may include feature points of the original signal o or the normalized original signal Onormal. The feature points may include points that can be features for distinguishing the original signal o or the normalized original signal Onormal from other signals.

Figure 5:
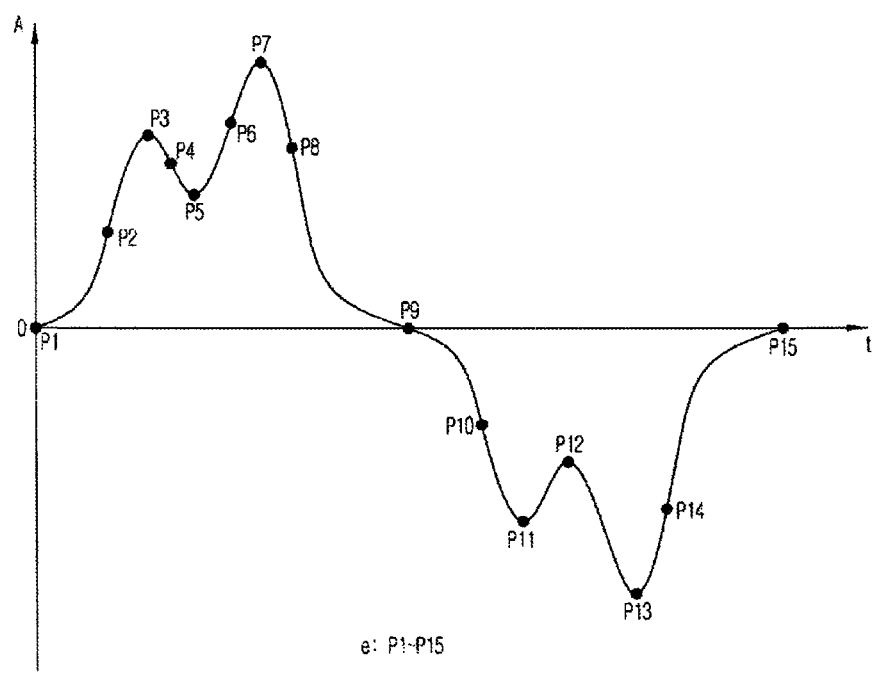
FIG. 5 is a view for describing a method of extracting feature points, according to some example embodiments.
Figure 6:
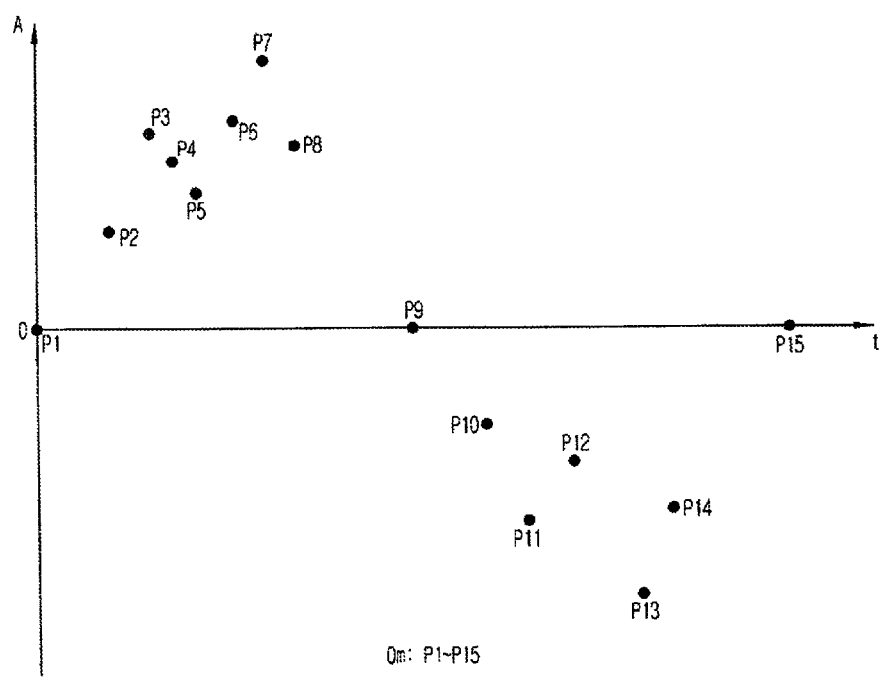
FIG. 6 is a view for describing an example of extracted feature points.

FIGS. 5 and 6 are views for describing a method of extracting feature points, according to some example embodiments.

In FIGS. 5 and 6, feature points extracted from the original signal o1 of the first period d1 are shown. However, feature points may be extracted from all the original signals o1, o2, and o2 of the respective periods d1, d2, and d3. According to some example embodiments, feature points may be extracted from a part of the original signal o, corresponding to a specific period, for example, from the original signal o1 corresponding to the first period d1 and the original signal o2 corresponding to the second period d2. According to other example embodiments, feature points may be extracted from the original signals f1, f2, and f3 corresponding to all periods of the normalized original signal Onormal. According to still other example embodiments, feature points may be extracted from normalized original signals (for example, the original signal f1 corresponding to the fourth period d4 and the original signal f3 corresponding to the fifth period d5) corresponding to predetermined periods of the normalized original signal Onormal.

As shown in FIG. 5, the feature points may include at least one of a start point p1 and an end point p15 of the first original signal o1. Also, the feature points may include at least one of points p3, p7, and p12 having relative maximum values of the first original signal o1, and points p5, p11, and p13 having relative minimum values of the first original signal o1. Also, the feature points may include at least one of the point p7 having the maximum value of the first original signal o1, and the point 13 having the minimum value of the first original signal o1. In addition, the feature points may include at least one of inflection points p2, p4, p6, p8, p9, p10, and p14 of the waves of the first original signal o1.

The data acquiring unit 123 (see FIG. 2) may extract at least one of the start point p1, the end point p15, the relative maximum value points p3, p7, and p12, the relative minimum value points p5, p11, and p13, and the inflection points p2, p4, p6, p8, p9, p10, and p14, as a feature point. For example, the data acquiring unit 123 may extract the start point p1, the relative maximum value points p3, p7, and p12, and the relative minimum value points p5, and p11, and p13 from the first original signal o1. As shown in FIG. 6, the data acquiring unit 123 may acquire signal-analyzed data e including the feature points p1 to p15. That is, the signal-analyzed data e may include information about the extracted feature points p1 to p15. The information about the individual feature points p1 to p15 may be at least ones of values (x-axis values) with respect to time of the individual feature points p1 to p15 and values (y-axis values) with respect to amplitude of the individual feature points p1 to p15.

Referring back to FIG. 2, the signal-analyzed data e acquired by the data acquiring unit 123 may be transferred to the reference data processor 130 or the transmission data generator 140.

The reference data processor 130 may generate reference data r or decide appropriate reference data r from the signal-analyzed data e acquired by the data acquiring unit 123. The reference data r generated by the reference data processor 130 may be transferred to reference data database 133. Alternatively, reference data r generated by the reference data processor 130 may be transferred to the reference data database 133, and reference data r decided by the reference data processor 130 may be transferred to the transmission data generator 140.

The reference data r is used by the reconstructing unit 200 to generate a reconstructed signal j based on the signal-analyzed data e.

Figure 7:
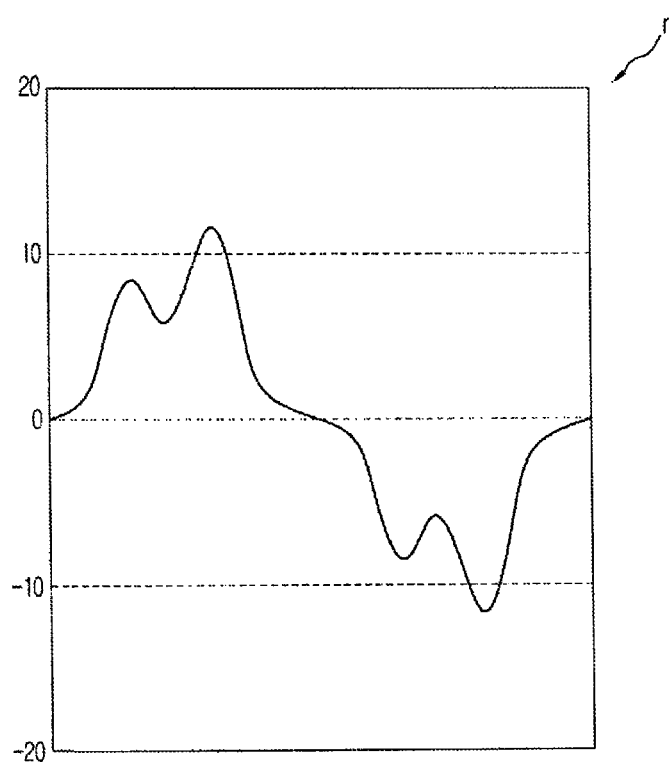
FIG. 7 is a graph showing an example of reference data.

FIG. 7 is a graph showing an example of reference data.

As shown in FIG. 7, reference data may be a waveform having a plurality of waves. The waves of the reference data may have a desired (or, alternatively, a predetermined) amplitude and a desired (or, alternatively, a predetermined) period. The reference data may have been defined in advance by a user according to the user's experience, or may be generated by a reference data generator 131. The reference data may have been stored in the reference data database 133.

As shown in FIG. 2, the reference data processor 130 may include the reference data generator 131 and a reference data decider 132. The reference data generator 131 may receive an original signal o from the signal output unit 110, and generate reference data r based on the received original signal o.

Figure 8:
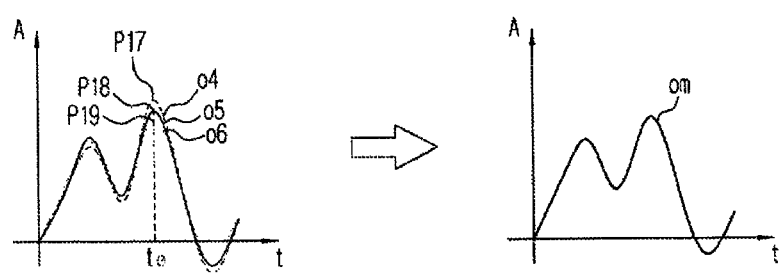
FIG. 8 is a view for describing a method of generating reference data, according to some example embodiments.

FIG. 8 is a view for describing a method of generating reference data, according to some example embodiments.

Referring to FIGS. 2 and 8, the reference data generator 131 may receive a plurality of different original signals o4, o5, and o6, and generate reference data r using the original signals o4, o5, and o6, as shown in FIG. 8. In this case, the reference data generator 131 may calculate an average value or an intermediate value of the original signals o4, o5, and o6 to generate the reference data r. More specifically, the reference data generator 131 may calculate an average value or an intermediate value of points p17, p18, and p19 on the original signals o4, o5, and o6 at an arbitrary time to, as shown in FIG. 8. If an average value or an intermediate value of corresponding points on the original signals o4, o5, and o6 is calculated every time or every period, a group of the calculated average values or a group of the calculated intermediate values may form a waveform om of waves, as shown in FIG. 8. The waveform om of waves may be reference data r. In this way, the reference data generator 131 may generate the reference data r. As another example, the reference data generator 131 may acquire maximum values or minimum values of the plurality of original signals o4, o5, and o6, and generate reference data r using a group of the maximum values or a group of the minimum values.

According to some example embodiments, the reference data generator 131 may determine whether to generate reference data r, based on the signal-analyzed data e received from the data acquiring unit 123. For example, the reference data generator 131 may receive the feature points detected from the original signal o from the data acquiring unit 123, and search for reference data r corresponding to the feature points in the reference data database 133. What reference data r corresponds to the feature points detected from the original signal o may be determined, for example, by comparing feature points of reference data r to the feature points detected from the original signal o to determine whether the feature points of the reference data r are identical or similar to the feature points detected from the original signal o. In this case, whether directions or magnitudes of changes between the feature points of the reference data r are identical or similar to directions or magnitudes of changes between the feature points detected from the original signal o may also be used to determine whether the reference data r corresponds to the feature points detected from the original signal o. If reference data r to which the received feature points correspond is found in the reference data database 133, the reference data generator 131 may generate no reference data r. However, if no reference data r to which the received feature points correspond is found in the reference data database 133, the reference data generator 131 may generate new reference data r. The generated reference data r may be stored in the reference data database 133.

The reference data decider 132 may decide reference data r corresponding to the signal-analyzed data e, based on at least one of the original signal o received from the signal output unit 110 and the signal-analyzed data e acquired by the data acquiring unit 123.

Figure 9:
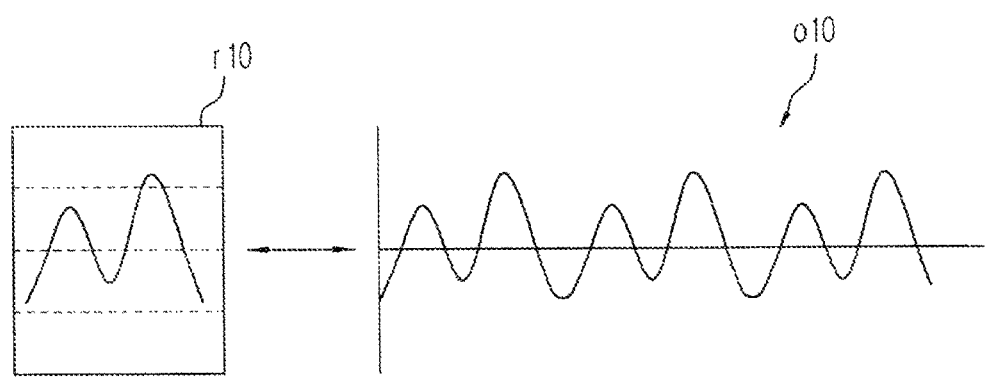
FIGS. 9 and 10 are views for describing a relationship between original data and reference data.
Figure 10:
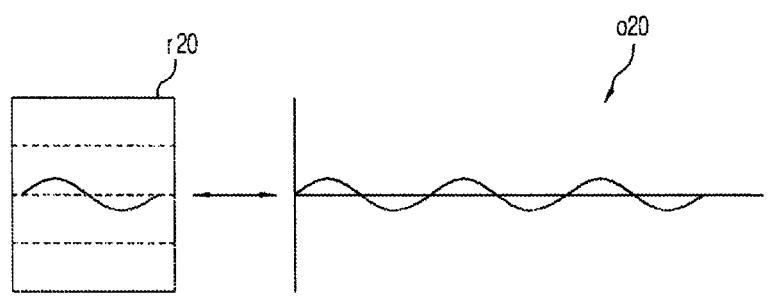

FIGS. 9 and 10 are views for describing a relationship between original data and reference data.

Referring to FIGS. 2, 9, and 10, according to some example embodiments, if the signal output unit 110 outputs original data o10 and o20 to the reference data processor 130, the reference data decider 132 may decide reference data r10 and r20 corresponding to the original data o10 and o20, based on the waveforms, periods, and/or amplitudes of the original data o10 and o20. The reference data decider 132 may decide one or more reference data r10 and r20 according to the received original data o10 and o20. If the reference data decider 132 receives original signals having the substantially same waveform, the substantially same period, and the substantially same amplitude, the reference data decider 132 may decide one reference data r. However, if the reference data decider 132 receives different original signals o10 and o20, as shown in FIGS. 9 and 10, the reference data decider 132 may decide two or more reference data r10 and r20. According to other example embodiments, the reference data decider 132 may compare feature points of the signal-analyzed data e to feature points of reference data, respectively, to detect reference data r having feature points that are identical or similar to the respective feature points of the signal-analyzed data e, thereby deciding the reference data r.

The reference data r may be transferred to the transmission data generator 140. The reference data decider 132 may call and receive the decided reference data r from the reference data database 133, and then transfer the received reference data r to the transmission data generator 140. Alternatively, the reference data decider 132 may decide reference data r, and then instruct the reference data database 133 to directly transfer the decided reference data r to the transmission data generator 140. The transmission data generator 140 may generate transmission data u, using the signal-analyzed data e received from the data acquiring unit 123 and the reference data r transferred from the reference data decider 132 or the reference data database 133. The transmission data u may be a packet including the signal-analyzed data e and the reference data r.

FIGS. 11 to 14 are views for describing various examples of packets that are generated using signal-analyzed data and reference data.

Figure 11:
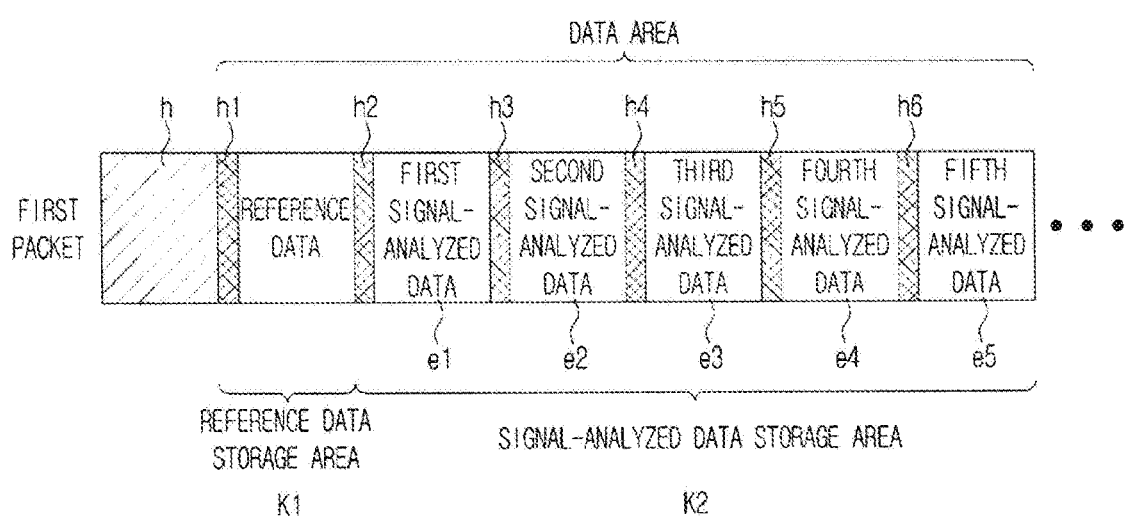
FIGS. 11 to 14 are views for describing various examples of packets that are generated using signal-analyzed data and reference data.

In FIG. 11, a first packet that is generated when there is one reference data r is shown. When there is one reference data r, the first packet may include a header h and a body (payload) following the header h, wherein the body may include a reference data storage area K1 and a signal-analyzed data storage area K2 following the reference data storage area K1.

The header h may be located at the foremost of a data block of data to be transmitted. The header h may include various kinds of information related to data stored in the body. The header h may include information, such as addresses of a transmitter and a receiver, or a communication protocol related to the format of data stored in the body, as necessary. The packet may be transmitted through a wired/wireless communication network based on information about the communication protocol. Also, the header h may include an electronic fingerprint or an electronic signature to inform a source of data stored in the body. If the header h includes an electronic fingerprint or an electronic signature, the reconstructing unit 200 (see FIG. 1) may determine what device the received transmission data u has been transmitted from. Accordingly, the reconstructing unit 200 may store reconstructed data j extracted from the transmission data u in a device that has transmitted the transmission data u, or the reconstructing unit 200 may transfer the reconstructed data j to another user terminal 300 (see FIG. 1).

The body may store various kinds of data. As shown in FIG. 11, the body may include the reference data storage area K1 and the signal-analyzed data storage area K2, the reference data storage area K1 may store reference data r decided by the reference data decider 132, and the signal-analyzed data storage area K2 may store a plurality of signal-analyzed data e1 to e5 output from the data acquiring unit 123. The signal-analyzed data storage area K2 may store the plurality of signal-analyzed data e1 to e5, as shown in FIG. 11, and each of the signal-analyzed data e1 to e5 may include at least one feature point. The reference data storage area K1 may be located ahead of the signal-analyzed data storage area K2, as shown in FIG. 11. However, the reference data storage area K1 may be located after the signal-analyzed data storage area K2. Meanwhile, a first header h1 may be provided ahead of reference data r of the reference data storage area K1. The first header h1 may include various information about the reference data r. The various information included in the first header h1 may include, for example, an identification number for identifying the reference data r. Also, second to sixth headers h2 to h6 including information about the signal-analyzed data e1 to e5 may be respectively provided ahead of the signal-analyzed data e1 to e5 stored in the signal-analyzed data storage area K2. The information included in the second to sixth headers h2 to h6 may include identification numbers for identifying the respective signal-analyzed data e1 to e5.

Figure 12:
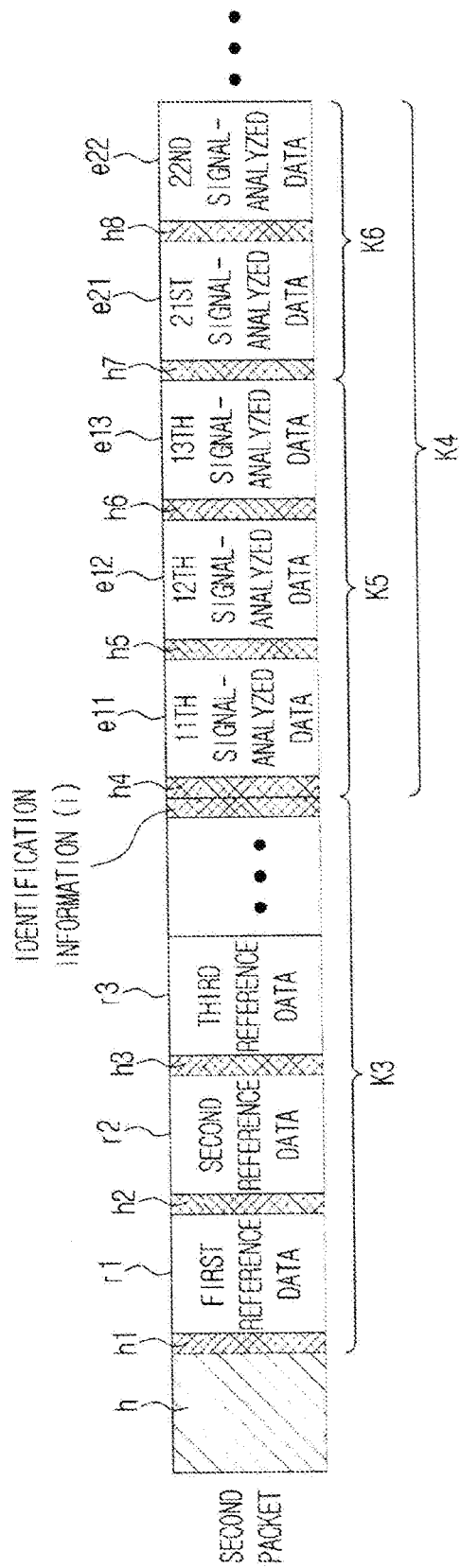
Figure 13:
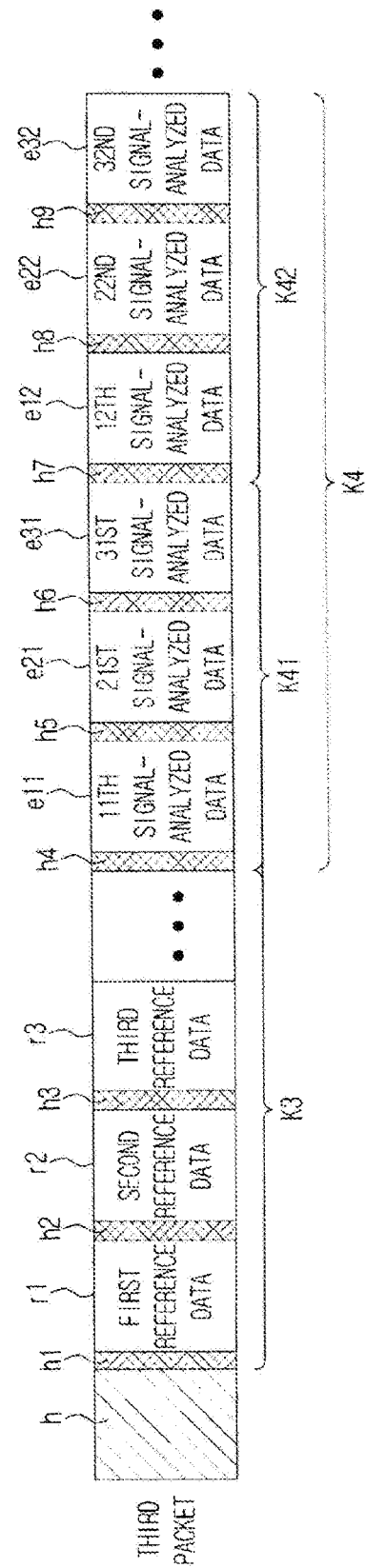
Figure 14:
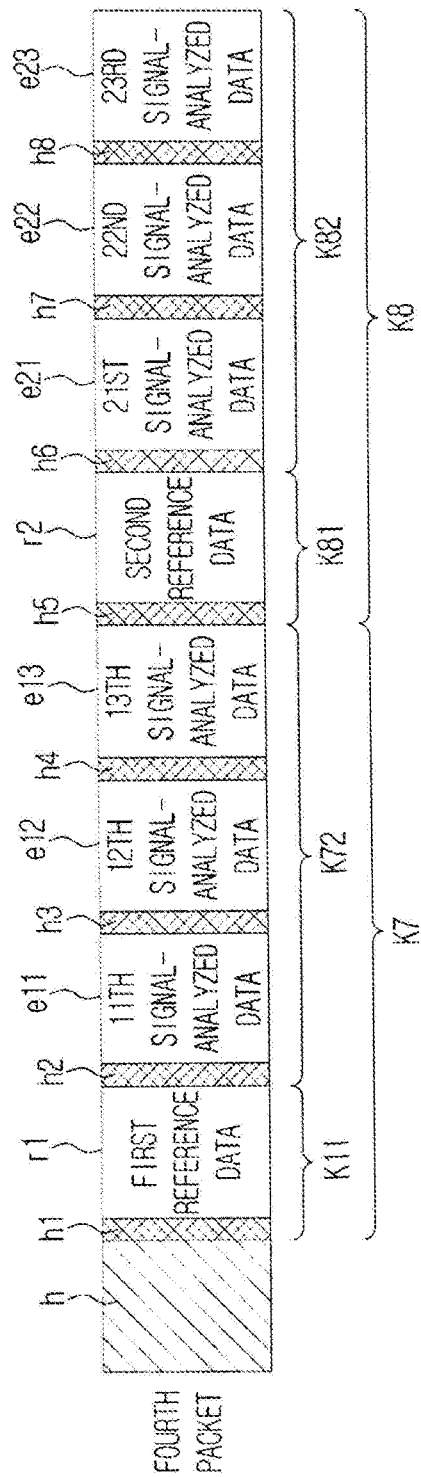

In FIGS. 12, 13, and 14, second, third, and fourth packets that are generated by the transmission data generator 140 (see FIG. 2) when there are a plurality of reference data r are shown. As shown in FIGS. 12, 13, and 14, the second, third, and fourth packets may include headers, like the first packet. The headers h of the second, third, and fourth packets may have the same configuration as the header h of FIG. 11.

As shown in FIG. 12, the second packet may include a reference data storage area K3 in which a plurality of reference data r1, r2, and r3 are stored, and a signal-analyzed data storage area K4 in which a plurality of signal-analyzed data e11 to e22 are stored. The signal-analyzed data storage area K4 may include a first signal-analyzed data storage area K5 in which the first signal-analyzed data is stored, and a second signal-analyzed data storage area K6 in which the second signal-analyzed data is stored.

A plurality of headers h1, h2, and h3 corresponding to the respective reference data r1, r2, and r3 may be provided ahead of the respective reference data r1, r2, and r3 of the reference data storage area K3. The respective headers h1, h2, and h3 may include information about the corresponding respective reference data r1, r2, and r3. The information about the respective reference data r1, r2, and r3, included in the respective headers h1, h2, and h3 may include identification numbers for identifying the respective reference data r1, r2, and r3. Also, the information about the respective reference data r1, r2, and r3, included in the respective headers h1, h2, and h3 may include information about which signal-analyzed data the respective reference data r1, r2, and r3 correspond to among the signal-analyzed data e11 to e22 stored in the signal-analyzed data storage areas K5 and K6. For example, the first header h1 of the first reference data r1 may include information informing that the first reference data r1 corresponds to 11th to 13th signal-analyzed data e11 to e13. According to other example embodiments, information about which signal-analyzed data the respective reference data r1, r2, and r3 correspond to among the signal-analyzed data e11 to e22 stored in the signal-analyzed data storage areas K5 and K6 may be stored in another area of the corresponding packet, instead of the headers h1, h2, and h3. For example, information informing that the first reference data r1 corresponds to the 11th signal-analyzed data e11 and the 12th signal-analyzed data e12 may be stored just ahead of or after a location at which the first reference data r1 is stored.

The first signal-analyzed data storage area K5 and the second signal-analyzed data storage area K6 of the second packet may store the corresponding signal-analyzed data, respectively. For example, the first signal-analyzed data storage area K5 may store the 11th to 13th signal-analyzed data e11 to e13, and the second signal-analyzed data storage area K6 may store the 21st and 22nd signal-analyzed data e21 and e22. The 11th to 13th signal-analyzed data e11 to e13 and the 21st and 22nd signal-analyzed data e21 and e22 may be distinguished by reference data r1 and r2 that are to be used upon reconstruction. The 11th to 13th signal-analyzed data e11 to e13 that are stored in the first signal-analyzed data storage area K5 may be stored in the order in which the 11th to 13th signal-analyzed data e11 to e13 have been acquired by the data acquiring unit 123. The first signal-analyzed data storage area K5 and the second signal-analyzed data storage area K6 may be arranged sequentially as shown in FIG. 12. In other words, when a plurality of reference data r1, r2, and r3 and signal-analyzed data e are packetized, the reference data r1, r2, and r3 and the signal-analyzed data e may be arranged in a packet such that signal-analyzed data e11 to e13 using the same reference data r1 is located close to each other, like the second packet shown in FIG. 12. Headers h4 to h8 including information about the respective signal-analyzed data e11 to e13 may be respectively provided ahead of the 11th to 13th signal-analyzed data e11 to e13 stored in the first signal-analyzed data storage area K5 and ahead of the 21st and 22nd signal-analyzed data e21 and e22 stored in the second signal-analyzed data storage area K6. Information included in the headers h4 to h8 may include information to identify the respective signal-analyzed data e11 to e22 or to determine which reference data r1, r2, or r3 the respective signal-analyzed data e11 to e22 corresponds to. In FIG. 12, an example in which three signal-analyzed data e11 to e13 are stored in the first signal-analyzed data storage area K5, and two signal-analyzed data e21 and e22 are stored in the second signal-analyzed data storage area K6 is shown.

However, the number of signal-analyzed data e11 to e22 that are stored in the respective signal-analyzed data storage areas K5 and K6 is not limited to this. Also, the number of reference data is not limited to three as shown in FIG. 12, and the number of reference data may be two or may be four or more.

As shown in FIG. 13, the third packet may include a reference data storage area K3 in which a plurality of reference data r1, r2, and r3 are stored, and a signal-analyzed data storage area K4 in which a plurality of signal-analyzed data e11 to e31 are stored. The reference data storage area K3 is the same as the reference data storage area K3 described above with reference to FIG. 12, and accordingly, a further description thereof will be omitted. The signal-analyzed data storage area K4 may include a third signal-analyzed data storage area K41 and a fourth signal-analyzed data storage area K42. Signal-analyzed data e11 to e31 and e12 to e32 stored in the respective signal-analyzed data storage areas K41 and K42 may be different from each other. In other words, 11th, 21st, and 31st signal-analyzed data e11, e21, and e31 stored in the third signal-analyzed data storage area K41, or 12th, 22nd, and 32nd signal-analyzed data e12 to e32 stored in the fourth signal-analyzed data storage area K42 may be different from each other. The 11th, 21st, and 31st signal-analyzed data e11, e21, and e31 that are different from each other may be distinguished by reference data r1 to r3 that are to be used upon reconstruction. In this case, the 11th, 21st, and 31st signal-analyzed data e11, e21, and e31 stored in the third signal-analyzed data storage area K41 may be data acquired earlier than the 12st, 22nd, and 32nd signal-analyzed data e12, e22, and e32 stored in the fourth signal-analyzed data storage area K42. In other words, the signal-analyzed data storage area K4 may arrange and store a plurality of signal-analyzed data e11 to e32 in the order in which the signal-analyzed data e11 to 32 have been acquired by the data acquiring unit 123. If the plurality of signal-analyzed data e11 to 32 are stored in the signal-analyzed data storage area K4, data can be sequentially packetized to generate transmission data u, and accordingly, a packetization rate can increase rather than that of the second packet. In FIG. 13, a case in which there are three reference data r1, r2, and r3 is shown, however, the number of reference data is not limited to three. Also, the kind and number of signal-analyzed data are not limited to those shown in FIG. 13.

Referring to FIG. 14, the fourth packet may include a first area K7 in which first reference data r1 and 11th to 13th signal-analyzed data e11 to e13 that can be reconstructed using the first reference data r1 are stored, and a second area K8 in which second reference data r1 and 21st to 23rd signal-analyzed data e21 to e23 that can be reconstructed using the second reference data r2 are stored. The first area K7 may include a first reference storage area in which the first reference data r1 is stored, and a third signal-analyzed data storage area K72 in which the 11th to 13th signal-analyzed data are stored. The first reference data storage area K71 may be located ahead of the 3rd signal-analyzed data storage section K72. According to other example embodiments, the first reference data storage area K71 may be located after the 3rd signal-analyzed data storage area K72. Likewise, the second area K8 may include a second reference data storage area K81 in which the second reference data r2 is stored, and a fourth signal-analyzed data storage area K82 in which the 21st to 23rd signal-analyzed data e21 to e23 are stored. In this case, the signal-analyzed data e11 to e13 that are reconstructed using the same reference data r1 are located close to the reference data r1 that is used to reconstruct the signal-analyzed data e11 to e13. The number of the areas K7 and K8 of the fourth packet, the number of the reference data r1 and r2 included in the areas K7 and K8, or the number of the signal-analyzed data e11 to e23 is also not limited to the corresponding number shown in FIG. 14. The fourth packet may include more areas than those shown in FIG. 14.

If transmission data u of a packet is acquired as shown in FIGS. 11 to 14, the data generator 100 (see FIG. 1) can transmit the transmission data u to the reconstructing unit 200 with low traffic using at least one of a wired communication network and a wireless communication network. Furthermore, the data generator 100 can store the transmission data u with a relatively small amount of storage space in a storage unit.

Referring back to FIG. 2, the transmission data u packetized and generated by the transmission data generator 140 may be transmitted to the reconstructing unit 200 through the communication unit 141, or stored temporarily or non-temporarily in the storage unit 142. The communication unit 141 may be a communication card or a communication chip that can perform wired communication or wireless communication. The storage unit 142 may be a disk storage device or a semiconductor memory storage device.

Referring back to FIG. 1, the reconstructing unit 200 shown in FIG. 1 may receive transmission data u transmitted from the data generator 100 through a wired/wireless communication network, and acquire a reconstructed signal based on the received transmission data u. According to some example embodiments, the reconstructing unit 200 may be included in at least one of a server computer, a desktop computer, a laptop computer, a smart phone, a cellular phone, a tablet PC, a Personal Digital Assistant (PDA), and a navigation system.

Figure 15:
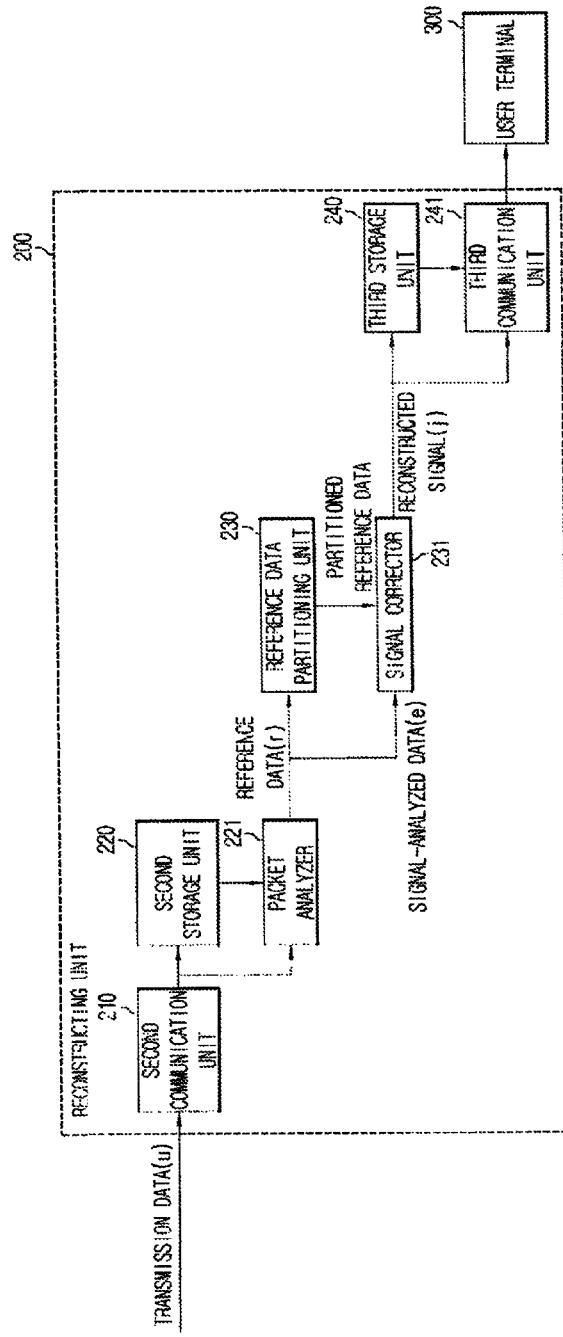
FIG. 15 is a block diagram of a reconstructing unit according to some example embodiments.

FIG. 15 is a block diagram of the reconstructing unit 200 according to some example embodiments.

As shown in FIG. 15, the reconstructing unit 200 may include a second communication unit 210, a second storage unit 220, a packet analyzer 221, a reference data partitioning unit 230, a signal corrector 231, a third storage unit 240, and a third communication unit 241.

The second communication unit 210 may receive the transmission data u transmitted from the first communication unit 141. The transmission data u may be transferred to the second storage unit 220 and/or the packet analyzer 221. The second storage unit 220 may temporarily or permanently store the transmission data u received by the second communication unit 210. The second storage unit 220 may be a disk storage device or a semiconductor memory device. The second storage unit 220 may function as a back-up storage space of the first storage unit 142. In other words, if the transmission data generator 140 stores the transmission data u in the first storage unit 142, the transmission data u may be transmitted to the reconstructing unit 200, and then stored in the second storage unit 220 for data back-up. If the transmission data u is a packet including signal-analyzed data e and reference data r, the packet analyzer 221 may analyze the packet to extract the signal-analyzed data e and the reference data r from the transmission data u.

Figure 16:
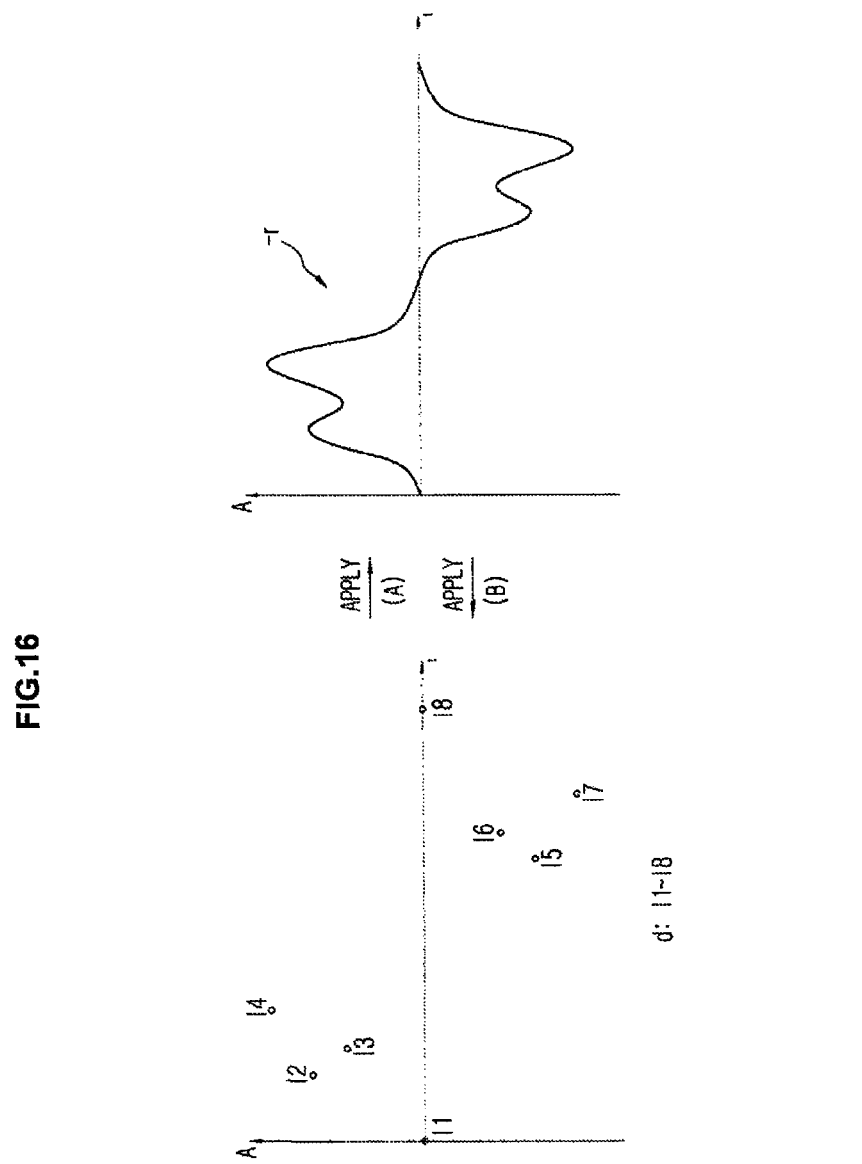
FIG. 16 is a view for describing reference data and signal-analyzed data analyzed from a packet.

FIG. 16 is a view for describing reference data and signal-analyzed data analyzed from a packet.

Referring to FIG. 16, the packet analyzer 221 may determine which reference data r corresponds to which signal-analyzed data e using headers h1 to h8 of the signal-analyzed data e and the reference data r. If reference data r and signal-analyzed data e corresponding to each other are decided by the packet analyzer 221, the reconstructing unit 200 may apply the signal-analyzed data e to the reference data r to correct the reference data r according to the signal-analyzed data e (A), or may estimate and reconstruct a waveform of signal from the signal-analyzed data e based on the reference data r (B), thereby acquiring a reconstructed signal j corresponding to an original signal o.

Hereinafter, a method of acquiring a reconstructed signal corresponding to an original signal o by applying signal-analyzed data e to reference data r to correct the reference data r according to the signal-analyzed data e will be described with reference to FIGS. 17 to 20.

Figure 17:
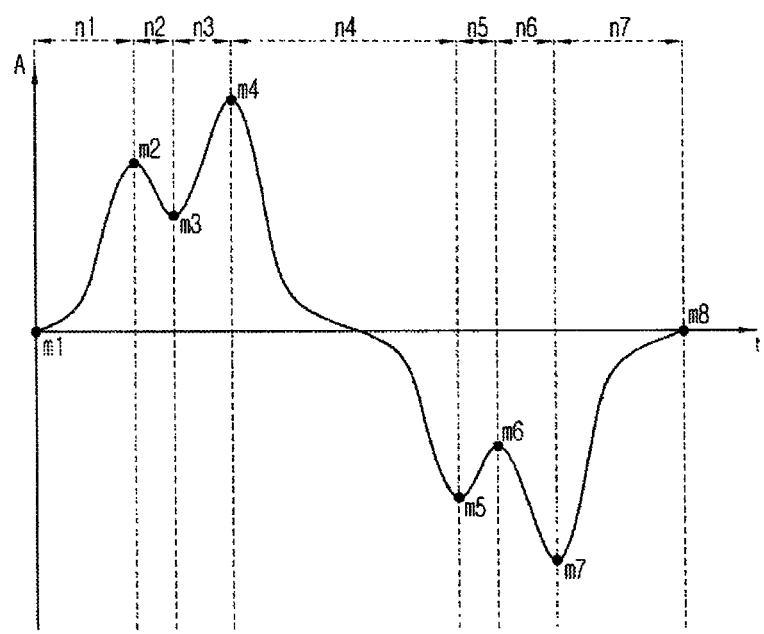
FIG. 17 is a view for describing a method of partitioning reference data, according to some example embodiments.

FIG. 17 is a view for describing a method of partitioning reference data, according to some example embodiments.

Referring to FIGS. 15 to 17, the packet analyzer 221 may transfer the extracted reference data r and the extracted signal-analyzed data e to the reference data partitioning unit 230. The reference data partitioning unit 230 may partition the reference data r into a plurality of areas n1 to n7 based on the signal-analyzed data e, as shown in FIG. 17. The reference data partitioning unit 230 may partition the reference data r into the plurality of areas n1 to n7 based on feature points of the signal-analyzed data e.

For example, as shown in FIG. 16, if the signal-analyzed data e includes a plurality of feature points 11 to 18, points m1 to m8 of the reference data r, corresponding to the plurality of feature points 11 to 18 may be detected from the reference data r. In this case, if the feature points 11 or 18 are a start point or an end point of the signal-analyzed data e, the points m1 and m8 of the reference data r, corresponding to the feature points 11 or 18 may be a start point or an end point of the reference data r. If the feature points 12 to 17 of the signal-analyzed data e are points having relative maximum values or relative minimum values, the points m2 to m7 of the reference data r, corresponding to the feature points 12 to 17 may be points having relative maximum values or relative minimum values. If the points m1 to m8 of the reference data e, corresponding to the feature points 11 to 18 of the signal-analyzed data e are acquired, the reference data r may be partitioned into a plurality of areas based on the points m1 to m8 corresponding to the feature points 11 to 18. As a result, a plurality of partitioned reference data may be acquired.

The plurality of partitioned reference data may be transferred to the signal corrector 231. According to some example embodiments, when the partitioned reference data is transferred to the signal corrector 231, the partitioned reference data may be temporarily stored in RAM installed in the reconstructing unit 220 for easiness of data processing.

Figure 18:
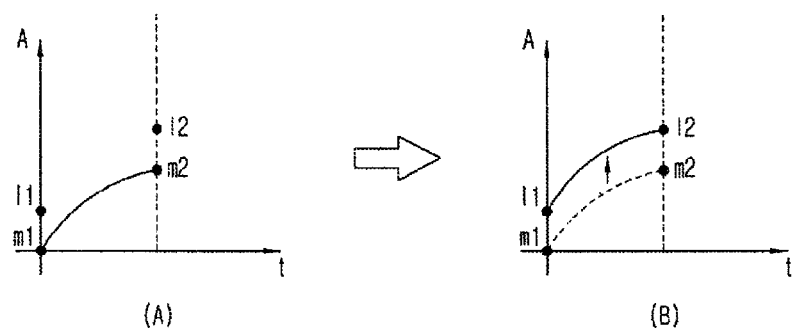
FIGS. 18 and 19 are views for describing methods of correcting partitioned reference data, according to some example embodiments.
Figure 19:
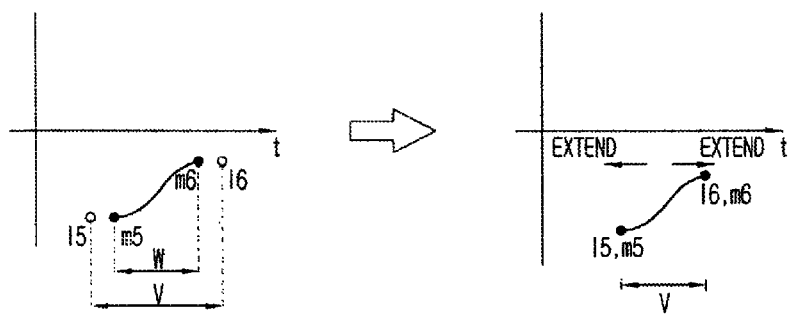
Figure 20:
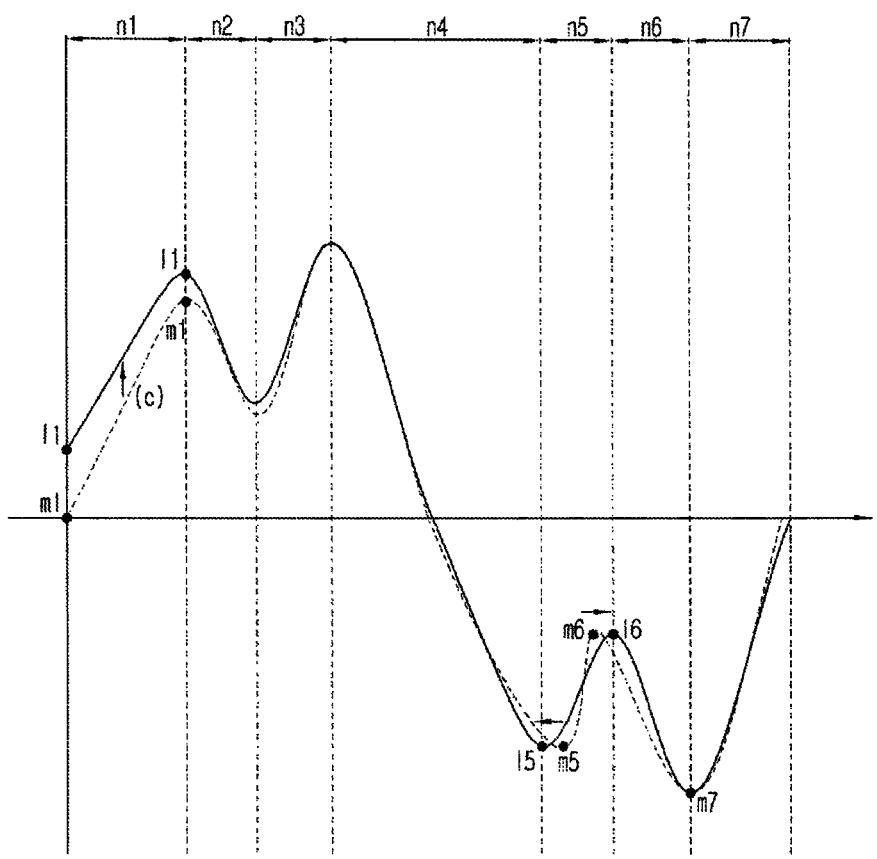
FIG. 20 is a graph showing an example of reconstructed data.

FIGS. 18 and 19 are views for describing various examples of a method of modifying and correcting partitioned reference data, and FIG. 20 shows an example of reconstructed data.

Referring to FIGS. 15, 18 and 19, the signal corrector 231 may receive the signal-analyzed data e from the packet analyzer 221, and receive the plurality of partitioned reference data from the packet data partitioning unit 230. The signal corrector 231 may modify the plurality of partitioned reference data using the signal-analyzed data e received from the packet analyzer 221 to thus acquire a plurality of partitioned, modified reference data. In this case, the signal corrector 231 may modify each partitioned reference data by moving the partitioned reference data or changing the size of the partitioned reference data. More specifically, the signal corrector 231 may modify each partitioned reference data by moving a location of the partitioned reference data corresponding to the signal-analyzed data e in at least one direction of x- and y-axes directions according to the signal-analyzed data e. Since the partitioned reference data has been partitioned based on the signal-analyzed data e, the location of the partitioned reference data corresponding to the signal-analyzed data e may be a start point m1 or m5 of the partitioned reference data, or an end point m2 or m6 of the partitioned reference data, as shown in FIGS. 18 and 19.

As shown in FIG. 18 (A), a start point 11 of signal-analyzed data may be spaced by a desired (or, alternatively, a predetermined) distance away from a start point m1 of partitioned reference data, corresponding to the start point 11. In this case, as shown in FIG. 18B, the signal corrector 231 may modify the partitioned reference data by moving the start point m1 of the partitioned reference data by the distance in an up direction. Likewise, if a point 12 having a relative maximum value of signal-analyzed data is spaced by a distance away from an end point m2 of partitioned reference data, corresponding to the point 12 having the relative maximum value, the signal corrector 231 may modify the partitioned reference data by moving the end point m2 of the partitioned reference data by the distance in an up direction. If the two points 11 and 12 have been spaced in the same direction away from the corresponding points m1 and m2 of the partitioned reference data, the entire of the partitioned reference data may move in the up direction, as shown in FIG. 18B.

As another example, as shown in FIG. 19, if a start point m5 and an end point m6 of partitioned reference data are located between a relative minimum value point 15 and a relative maximum value point 16 of signal-analyzed data, respectively corresponding to the start point m5 and the end point m6, the signal corrector 231 may modify the partitioned reference data by moving the start point m5 and the end point m6 of the partitioned reference data to the relative minimum value point 15 and the relative maximum value point 16, respectively. In this case, the partitioned reference data may extend in a left-right direction, as shown in FIG. 19. According to some example embodiment, the signal corrector 231 may calculate a distance v between the relative minimum value point 15 and the relative maximum value point 16 of the signal-analyzed data, and a distance w between the start point m5 and the end point m6 of the partitioned reference data, acquire a scaling ratio of the distances v and w, and then extend or reduce the partitioned reference data according to the scaling ratio, thereby modifying the partitioned reference data. In FIG. 19, a case of extending or reducing partitioned reference data in the x-axis direction is shown, however, the partitioned reference data may extend or be reduced in the y-axis direction.

The signal corrector 231 may combine the partitioned reference data to acquire a reconstructed signal as shown in FIG. 20. In this case, the entire or a part of the combined, partitioned reference data may be partitioned reference data modified according to the signal-analyzed data e as shown in FIGS. 18 and 19. According to some example embodiments, the combined, partitioned reference data may be partitioned reference data that has been never modified.

The reconstructed signal acquired by the signal corrector 231 may be transferred to the third storage unit 240 and/or the third communication unit 241. The third storage unit 240 may temporarily or permanently store the reconstructed signal. According to some example embodiments, the third storage unit 240 may be the same device as the second storage unit 220. The third communication unit 241 may transfer the reconstructed signal to another user terminal 300. The third communication unit 241 may be the same device as second communication unit 210.

In the system of transmitting and reconstructing data, the data generator 100 may be configured to generate transmission data and transmit the transmission data to the reconstructing unit 200, and the reconstructing unit 200 may be configured to receive the transmission data and reconstruct the received data as described above. However, the data generator 100 is not only applied to a system of transmitting and reconstructing data. Also, the transmission data generated by the data generator 100 is not necessarily transmitted.

For example, the data generator 100 may be used in a data retention system. In this case, the data generator 100 may acquire signal-analyzed data e and reference data r corresponding to the signal-analyzed data e, and then packetize the signal-analyzed data e and the reference data r, as described above, in order to store and retain data. The packetized data may be stored in a storage unit such as a semiconductor memory device installed in the data generator 100. The data stored in the storage unit may be reconstructed by the reconstructing unit 200. The device performing the functions of the data generator 100 may be same device as the device performing the functions of the reconstructing unit 200. That is, a computer device that has generated packetized data may be a computer device that reconstructs the packetized data.

The system of converting and reconstructing signals, as described above, may be applied to various kinds of systems. For example, the system of converting and reconstructing signals may be applied to a system of acquiring walking information from a walking assistance robot, and storing, transmitting, and managing the walking information. Also, the system of converting and reconstructing signals may be applied to a system of acquiring vehicle driving information from a vehicle, and storing, transmitting, and managing the vehicle driving information. Also, the system of converting and reconstructing signals may be applied to various kinds of systems configured to perform a function of recording and transmitting operations of various devices.

Hereinafter, a system (hereinafter, a walking management system) configured to manage walking of a wearer of a walking assistance robot will be described with reference to FIGS. 21 to 24.

Figure 21:
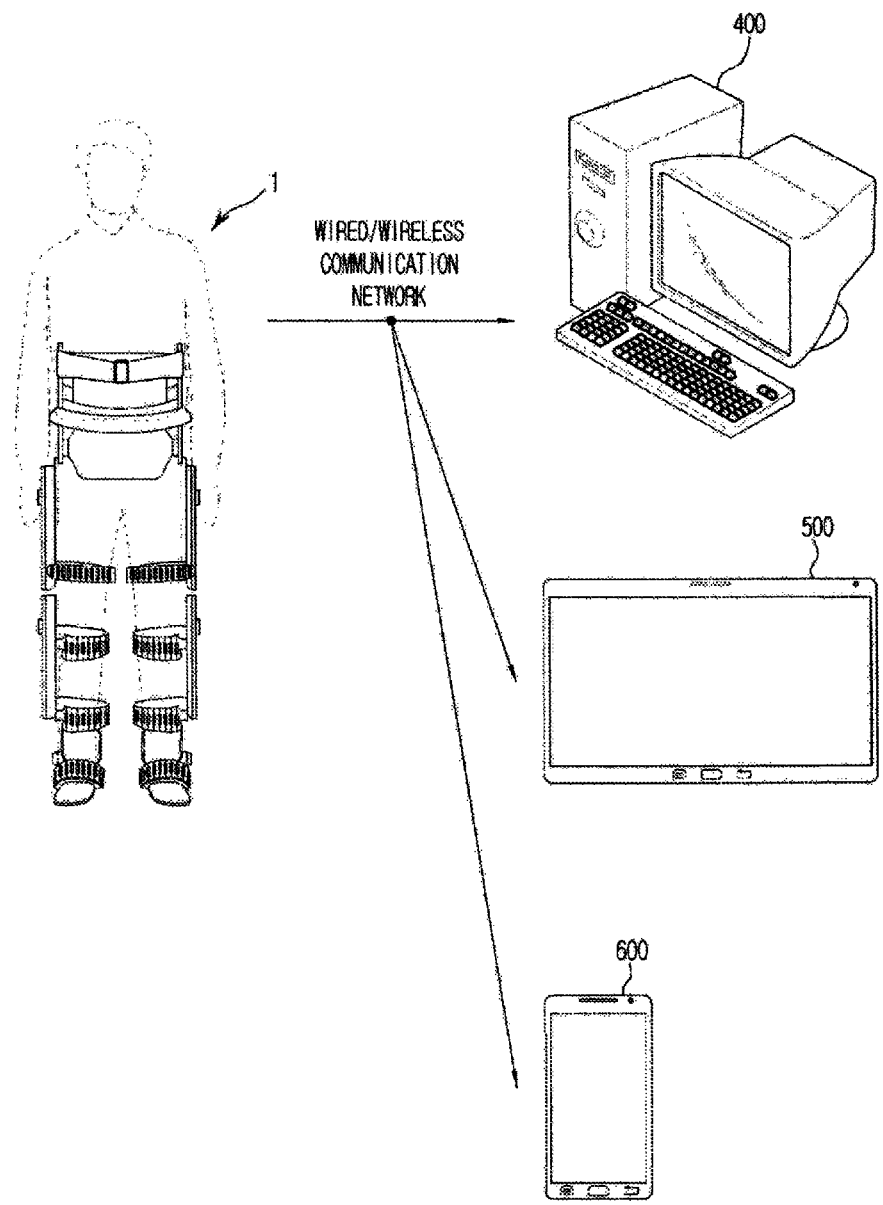
FIG. 21 illustrates a walking management system according to some example embodiments.

FIG. 21 shows a walking management system according to some example embodiments.

Referring to FIG. 21, the walking management system may include a walking assistance robot 1, and various data processors 400, 500, and 600 that can transmit/receive data to/from the walking assistance robot 1 through a wired/wireless communication network. The walking assistance robot 1 may be secured and worn on a part of a wearer's body. For example, the walking assistance robot 1 may be secured and worn on at least one of a wearer's left and right legs. The walking assistance robot 1 may apply a desired (or, alternatively, a predetermined) force to a desired (or, alternatively, a predetermined) part of the wearer's body to thus help the wearer's walking. At least one of the data processors 400, 500, and 600 may be a server. The wired/wireless communication network has been described above with reference to FIG. 1.

Figure 22:
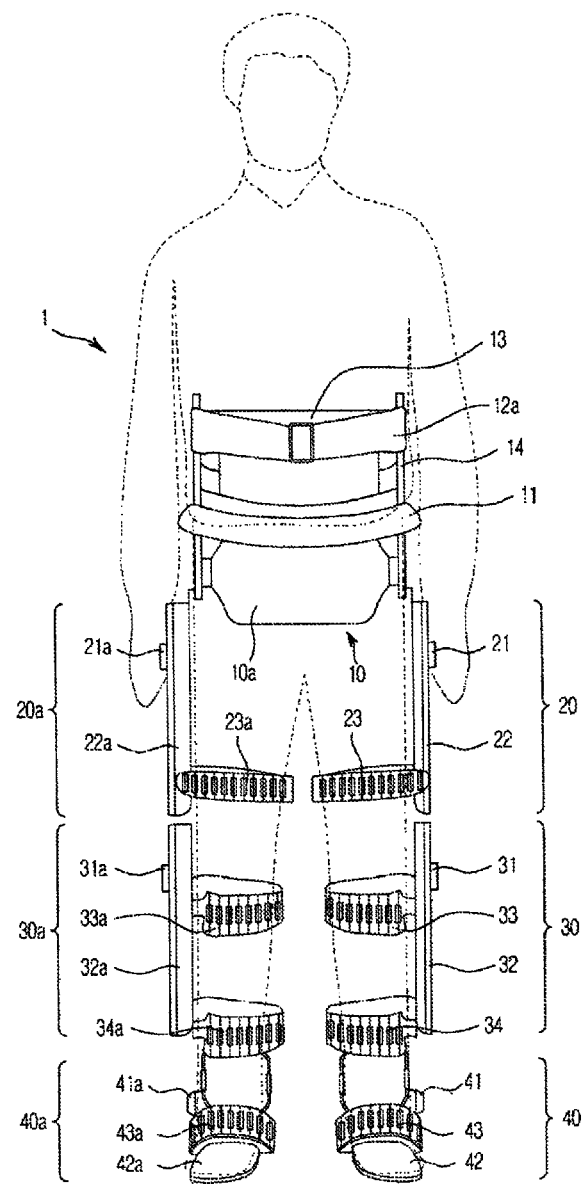
FIG. 22 is a front view of a walking assistance robot according to some example embodiments.
Figure 23:
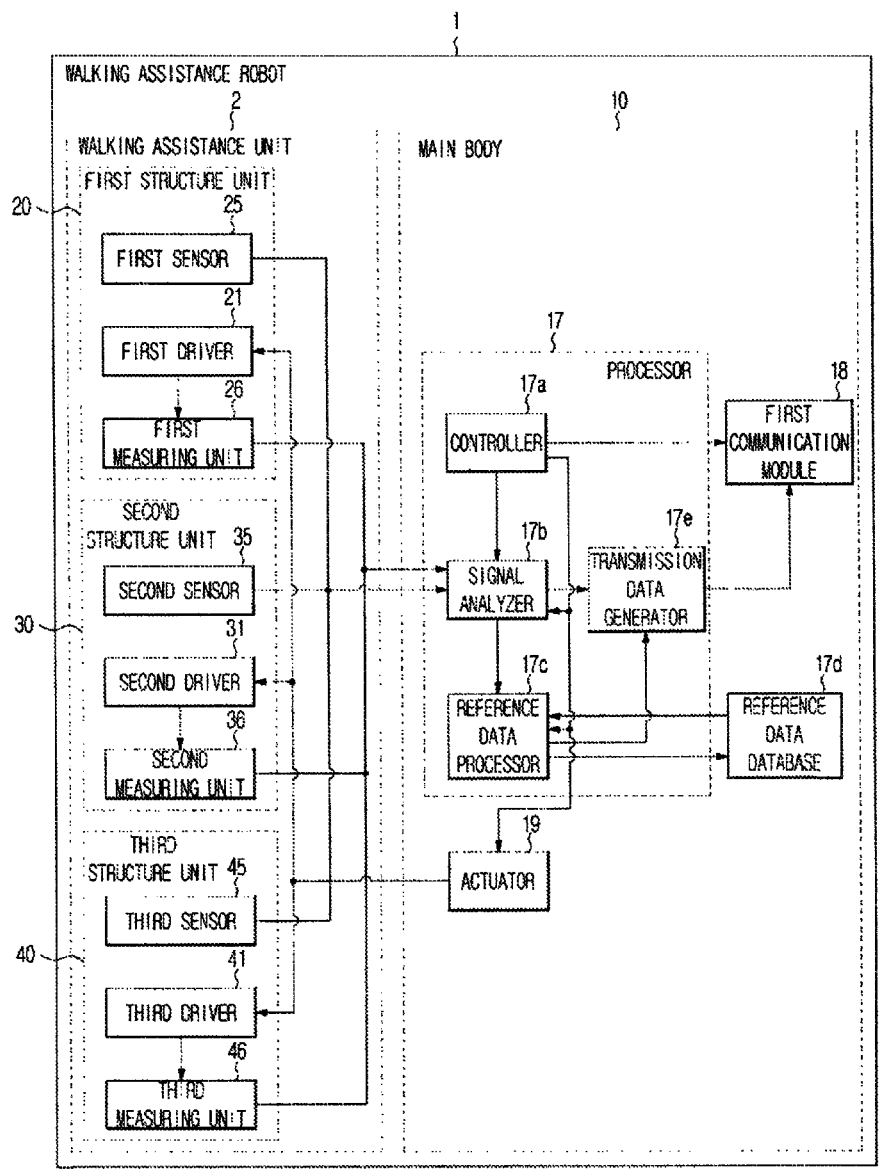
FIG. 23 is a block diagram of a walking assistance robot according to some example embodiments.

FIG. 22 is a front view of the walking assistance robot 1 according to some example embodiments, and FIG. 23 is a block diagram of the walking assistance robot 1 according to some example embodiments.

As shown in FIGS. 22 and 23, the walking assistance robot 1 may include a walking assistance unit 2 that is worn on the entire or a part of a leg or foot of a wearer who has worn the walking assistance robot 1 to help the wearer's walking, and a main body 10 in which elements for controlling the walking assistance unit 2 are installed.

The walking assistance unit 2 may include at least one of a first structure unit 20, a second structure unit 30, and a third structure unit 40, as shown in FIGS. 22 and 23. Hereinafter, the walking assistance robot 1 is assumed to include all of the first structure unit 20, the second structure unit 30, and the third structure unit 40. However, example embodiments are not limited thereto, and the walking assistance robot 1 may include a part of the first structure unit 20, the second structure unit 30, and the third structure unit 40. Also, the walking assistance robot 1 may further include a fourth structure unit in addition to the first to third structure units 20, 30, and 40.

According to some example embodiments, the walking structure unit 2 may include a single first structure unit 20, a single second structure unit 30, and a single third structure unit 40. In this case, at least one of the first structure unit 20, the second structure unit 30, and the third structure unit 40 may be worn on any one of the wearer's left and right legs. According to other example embodiments, the walking assistance unit 2 may include a pair of first structure units 20 and 20a, a pair of second structure units 30 and 30a, and a pair of third structure units 40 and 40a to be respectively worn on both the wearer's left and right legs, as shown in FIG. 22. Although the walking assistance unit 2 includes a pair of first structure units 20 and 20a, a pair of second structure units 30 and 30a, and a pair of third structure units 40 and 40a, the functions or operations of the corresponding structure units 20 and 20a, 30 and 30a, and 40 and 40a may be substantially the same with negligible differences while the respective structure units 20, 30, and 40 have different driving directions. According to other example embodiments, the walking assistance unit 2 may include a part of the first to third structure units 20 to 40 as a single unit, and the other part of the first to third structure units 20 to 40 as a pair of units. For example, the walking assistance unit 2 may include a pair of first structure units 20 and 20a, a single second structure unit 30, and a single third structure unit 40.

The first structure units 20 and 20a may assist motions of the wearer's femoral regions and hip joints upon walking. The first structure units 20 and 20a may include one or more first drivers 21 and 21a and one or more first supporting units 22 and 22a.

The first drivers 21 and 21a may generate various magnitudes of torque according to a control command transferred from a processing unit 17 of the main body 10 or according to driving of an actuator 19, and apply the generated torque to the first supporting units 22 and 22a. The magnitude of torque that is applied to the first supporting units 22 and 22a may be constant or vary. While applying various magnitudes of torque to the first supporting units 22 and 22a, the first drivers 21 and 21a may rotate in at least one direction. The rotation range of the first drivers 21 and 21a may be in the Range Of Motion (ROM) of the wearer's hip joints.

According to some example embodiments, the first drivers 21 and 21a may include at least one motor for generating a desired (or, alternatively, a predetermined) magnitude of torque according to electrical energy supplied from a power supply installed in the main body 10. The at least one motor may be a motor having an encoder. According to other example embodiments, the first drivers 21 and 21a may include at least one piston or at least one cylinder device that generates torque by operating by electrical energy or fluid pressure (e.g., oil pressure or air pressure) supplied from the main body 10. According to still other example embodiments, the first drivers 21 and 21*a* may include all of at least one motor and at least one piston or at least one cylinder device.

The first supporting units 22 and 22*a* may connect to the first drivers 21 and 21*a*, and rotate in at least one direction according to torque generated by the first drivers 21 and 21*a*. The first supporting units 22 and 22*a* may be implemented in various structures according to a designer of the walking assistance robot 1. For example, the first supporting units 22 and 22*a* may include at least one supporting plate. As another example, each of the first supporting units 22 and 22*a* may include a plurality of nodes, and at least one link connecting the plurality of nodes to each other. Each node may be a supporting bar or a supporting panel. The first supporting units 22 and 22*a* may include one or more first securing parts 23 and 23*a*. The first supporting units 22 and 22*a* may be secured on the outer or inner side of the wearer's femoral regions through the first securing parts 23 and 23*a*.

The first supporting units 22 and 22*a* may apply a desired (or, alternatively, a predetermined) magnitude of torque generated by the first drivers 21 and 21*a* to the wearer's femoral regions through the first securing units 23 and 23*a*. More specifically, if the first supporting units 22 and 22*a* rotate in a direction according to driving of the first drivers 21 and 21*a*, the wearer's femoral regions on which the first supporting units 22 and 22*a* are secured by the first securing units 23 and 23*a* may also rotate in the same direction. As a result, the first structure units 20 and 20*a* may apply the magnitude of torque to the wearer's femoral regions or hip joints in order to assist the wearer's motion of raising or lowering his/her femoral regions. Accordingly, the wearer can be assisted by the walking assistance robot 1 when raising his/her legs or walking.

The first securing units 23 and 23*a* may be made of a metal material or an elastic material such as rubber. Each of the first securing units 23 and 23*a* may include at least one of a chain, a band having elasticity, and various kinds of straps. Also, the first securing units 23 and 23*a* may be any other securing means that can be considered by one of ordinary skill in the art in order to secure the first supporting units 22 and 22*a* on a wearer's femoral regions.

The second structure units 30 and 30*a* may assist motions of the wearer's lower legs and knee joints upon walking. The second structure units 30 and 30*a* may include second drivers 31 and 31*a*, second supporting units 32 and 32*a*, and second securing units 33 and 33*a*, as shown in FIGS. 22 and 23. Also, the second structure units 30 and 30*a* may include second securing units 33, 34, 33*a*, and 34*a* to fix the second structure units 30 and 30*a* on the wearer's thighs. The configuration, structure, and material of the second structure units 30 and 30*a* may be the same as or different from those of the first structure units 20 and 20*a* described above.

The third structure units 40 and 40*a* may assist motions of the wearer's ankles. The third structure units 40 and 40*a* may include third drivers 41 and 41*a*, foot rest units 42 and 42*a*, and third securing units 43 and 43*a*. The soles of the wearer's feet may be rested on the foot rest units 42 and 42*a*. Each of the foot rest units 42 and 42*a* may include a weight sensor for sensing a wearer's weight to determine whether the wearer has worn the walking assistance robot 1 or whether the wearer has stood up. Also, each of the foot rest units 42 and 42*a* may include a Ground Reaction Force (GRF) sensor for sensing a GRF that is transferred to the wearer's foot when the wearer is walking. The configuration, structure, and material of the third structure units 40 and 40*a* may be the same as or different from those of the first structure units 20 and 20*a* or the second structure units 30 and 30*a*.

The first to third structure units 20 to 40 may operate according to power received from the actuator 19 installed in the main body 10.

Figure 24:
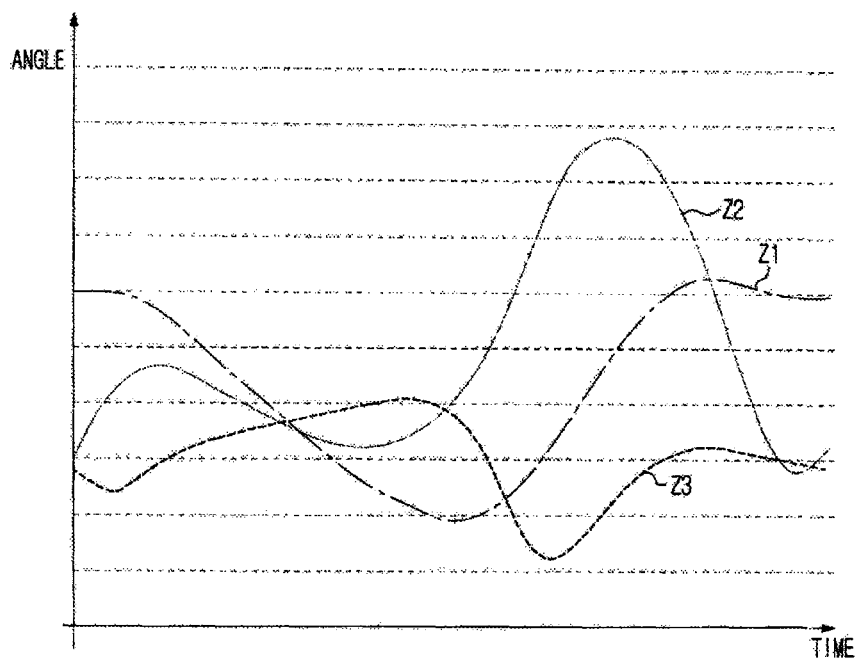
FIG. 24 is a graph showing walking signals output from individual drivers of a walking assistance robot.

FIG. 24 shows walking signals that are output from individual drivers of the walking assistance robot 1.

Referring to FIGS. 22 to 24, the first to third structure units 20 and 20*a* to 40 and 40*a* may output walking signals that change according to the wearer's walking.

The first structure unit 20, the second structure unit 30, and the third structure unit 40 may include a first sensor 25, a second sensor 35, and a third sensor 45, respectively. The first sensor 25 may sense motions of at least one of the first driver 21, the first supporting unit 22, and the wearer's hip joint. More specifically, the first sensor 25 may sense at least one of motions of the first driver 21, the first supporting unit 22, and the wearer's hip joint, and convert the sensed motion into an electrical signal to acquire a hip joint walking signal z1 as shown in FIG. 24. The hip joint walking signal z1 may be transferred to the processing unit 17 of the main body 10. The hip joint walking signal z1 may represent at least one of a joint angle of the corresponding hip joint, a slope of the corresponding first supporting unit 22, and an angular velocity and angular acceleration of the first supporting unit 22 or the hip joint. The second sensor 35 may sense at least one of motions of the second driver 31, the second supporting unit 33, and the wearer's knee joint, and convert the sensed motion into an electrical signal to acquire a knee joint walking signal z2. The knee joint walking signal z2 may represent at least one of a joint angle of the corresponding knee joint, a slope of the corresponding second supporting unit 32, and an angular velocity and angular acceleration of the second supporting unit 32 or the knee joint. The third structure unit 40 may include the third sensor 45 as shown in FIG. 23. The third sensor 45 may sense at least one of motions of the third driver 41, the third supporting unit 43, and the wearer's ankle joint, and convert the sensed motion into an electrical signal to acquire an ankle joint walking signal z3. The ankle joint walking signal z3 may represent at least one of a joint angle of the corresponding ankle joint, a slope of the corresponding third supporting unit 42, and an angular velocity and angular acceleration of the third supporting unit 42 or the ankle joint. Each of the first sensor 25, the second sensor 35, and the third sensor 45 may be at least one of a joint angle sensor, a tilt sensor, an acceleration sensor, and an Inertial Measurement Unit (IMU).

The first sensor 25 may be installed in at least one of the first drivers 21 and 21*a* and the second supporting units 22 and 22*a*. Alternatively, a part of the first sensor 25 may be installed in the first driver 21, and the other part of the first sensor 25 may be installed in the first supporting unit 22. For example, a joint angle sensor may be installed in the first driver 21, and a tilt sensor or an IMU may be installed in the first supporting unit 22. The second sensor 35 may be installed in at least one of the second drivers 31 and 31*a* and the second supporting units 32 and 32*a*. Alternatively, a part of the second sensor 35 may be installed in the second driver 31, and the other part of the second sensor 35 may be installed in the second supporting unit 32. The third sensor 45 may also be installed in at least one of the third drivers 41 and 41 and the third supporting units 42 and 42*a*. Alternatively, a part of the third sensor 45 may be installed in the third driver 41, and the other part of the third sensor 45 may be installed in the third supporting unit 42 or in both the third driver 41 and the third supporting unit 42.

The first structure unit 20 may include at least one first measuring unit 26 as shown in FIG. 23. The first measuring unit 26 may measure information about operations of the first driver 21, received from the first driver 21. If the first driver 21 is a motor having an encoder, the first measuring unit 26 may measure information about an operation of the first driver 21 using an encoder value of the encoder. The first measuring unit 26 may output the hip joint walking signal z1 according to the results of the measurement, as shown in FIG. 24. The hip joint walking signal z1 may represent at least one of a joint angle, an angular velocity, and angular acceleration of the first driver 21. Various parameters measured by the first measuring unit 26 may be transferred to the processing unit 17, as shown in FIG. 23. The second structure unit 30 may also include at least one second measuring unit 36, as shown in FIG. 23. The second measuring unit 36 may measure information about an operation of the second driver 31. If the second driver 31 is a motor having an encoder, the second measuring unit 36 may measure information about an operation of the second driver 31 using an encoder value from the encoder. Various parameters measured by the second measuring unit 36 may be transferred to the signal analyzer 17b as shown in FIG. 23. The third structure unit 40 may also include at least one third measuring unit 46. The third measuring unit 46 may measure information about an operation of the third driver 41, and transfer the measured information to the signal analyzer 17b. If the third driver 41 is a motor having an encoder, the third measuring unit 46 may measure an angle, a velocity, and acceleration of a joint using an encoder value from the encoder.

The main body 10 may control operations of the walking supporting unit 2. The main body 10 may include a main body housing 10a that can accommodate various components for controlling the walking assistance robot 1, as shown in FIG. 22. The main body housing 10a may include a Printed Circuit Board (PCB) on which processors for performing functions of the processing unit 17 can be mounted, and a power supply for supplying power to the processors or the actuator 19. The main body housing 10a of the main body 10 may stably fix the components accommodated therein while securely protecting the components.

The main body 10 may further include a first waist securing unit 11 and a second waist securing unit 12a. The first and second waist securing units 11 and 12a may secure the main body housing 10a on a part (e.g., a waist) of the wearer's body. The first waist securing unit 11 may connect, for example, to the main body housing 10a, and the second waist securing unit 12a may connect to a first waist supporting unit 13. The first and second waist securing units 11 and 12a may be bands having elasticity and various kinds of straps. Also, the first and second waist securing units 11 and 12a may be any other securing means that can be considered by one of ordinary skill in the art in order to fix the main body housing 10a on the wearer's waist or hips. The main body 10 may further include the first waist supporting unit 13 to support the wearer's waist. The first waist supporting unit 13 may be designed in a shape corresponding to the wearer's waist in order to support the wearer's waist. The first waist supporting unit 13 may connect to a second waist supporting unit 14 provided outside the main body housing 10a, as shown in FIG. 22.

The main body 10 may include the processing unit 17, a first communication module 18, and the actuator 19, as shown in FIG. 23.

The processing unit 17 may control overall operations of the walking assistance robot 1, and generate transmission data to be stored or transmitted, based on a walking signal output from the first to third sensors 25 to 45 or a walking signal output from the first to third measuring units 26 to 46.

The processing unit 17 may be implemented as a processor that is installed in the main body housing 10a. The processor may be a processing device in which an Arithmetic Logic Unit (ALU), a register, a program counter, a command decoder, a control circuit, etc. are installed in at least one silicon chip. Also, the processor may be at least one semiconductor chip mounted on a predetermined PCB installed in the housing 10a.

The processing unit 17 may include a controller 17a, the signal analyzer 17b, a reference data processor 17c, and a transmission data generator 17e.

The controller 17a may control overall operations of the walking assistance robot 1 by controlling the signal analyzer 17b, the reference data processor 17c, the transmission data generator 17e, the first communication module 18, and the actuator 19 in the processing unit 17.

The controller 17a may generate a control signal for controlling a target to be controlled, and transfer the control signal to the target so that the target operates according to the control signal.

The signal analyzer 17b may receive the walking signals z1, z2, and z3, and analyze the walking signals z1, z2, and z3 to acquire signal-analyzed data. The walking signals z1, z2, and z3 may be output from the first to third sensors 25 to 45 or from the first to third measuring units 26 to 46. The signal analyzer 17b may determine whether the walking signals z1, z2, and z3 are signals capable of acquiring signal-analyzed data. Also, the signal analyzer 17b may determine whether to acquire signal-analyzed data from the walking signals z1, z2, and z3.

The signal analyzer 17b may normalize the walking signals z1, z2, and z3 to acquire normalized walking signals. For example, if the walking signals z1, z2, and z3 have changing periods, the signal analyzer 17b may change the periods of the walking signals z1, z2, and z3 such that the walking signals z1, z2, and z3 have a constant period, thereby acquiring normalized walking signals.

The signal analyzer 17b may acquire signal-analyzed data from the walking signals z1, z2, and z3 or from the normalized walking signals. The signal-analyzed data may include feature points of the walking signals z1, z2, and z3 or the normalized walking signals. The feature points may include at least one of a start point, an end point, a waveform relative maximum value, a waveform relative minimum value, and a waveform inflection point of the walking signals z1, z2, and z3 or the normalized walking signals. The signal-analyzed data acquired by the signal analyzer 17b may be transferred to the transmission data generator 17e. The signal-analyzed data acquired by the signal analyzer 17b may be transferred to the reference signal processor 17c as necessary.

The reference data processor 17c may generate reference data, or reference data corresponding to the signal-analyzed data acquired by the signal analyzer 17b. The reference data processor 17c may receive the walking signals z1, z2, and z3 from the first to third sensors 25 to 45 or from the first to third measuring units 26 to 46, and generate reference data based on the walking signals z1, z2, and z3. The reference data processor 17c may partition a walking signal output from the same path, for example, the hip joint walking signal z1 output from the first sensor 25 every period to acquire a plurality of partitioned hip joint walking signals, and calculate an average value or an intermediate value of the plurality of partitioned hip joint walking signals to generate reference data. The reference data may be transferred to and stored in the reference data database 17d.

The reference data processor 17c may determine whether reference data r corresponding to the signal-analyzed data exists in the reference data database 17d, based on the signal-analyzed data received from the signal analyzer 17b, and determine whether to generate the reference data r according to the result of the determination. The reference data processor 17c may determine reference data r corresponding to the signal-analyzed data, based on at least one of the walking signals z1, z2, and z3 output from the first to third sensors 25 to 45 or the first to third measuring units 26 to 46 and the signal-analyzed data acquired by the signal analyzer 17b. For example, the reference data processor 17c may decide reference data r corresponding to the walking signals z1, z2, and z3 with reference to the waveforms, periods, and amplitudes of the walking signals z1, z2, and z3. Also, the reference data processor 17c may decide reference data r corresponding to the walking signals z1, z2, and z3 using the feature points of the walking signals z1, z2, and z3. The reference data r may be transferred to the transmission data generator 17e.

The transmission data generator 17e may generate transmission data using the signal-analyzed data received from the signal analyzer 17b and the reference data r received from the reference data decider 17c or the reference data database 17d. The transmission data may be acquired by packetizing the signal-analyzed data and the reference data r. The signal-analyzed data and the reference data r may be packetized in such formats as shown in FIGS. 11 to 14. The transmission data may be transferred to the first communication module 18, and the first communication module 18 may transfer the transmission data to the data processors 400 to 600 (see FIG. 21) through a wired/wireless communication network. According to an embodiment, the transmission data may be temporarily or permanently stored in a storage unit, such as a disk storage unit or a semiconductor memory device installed in the main body housing 10a.

According to some example embodiments, the main body 10 may further include a sensor for sensing a wearer's various motions to collect various information related to the wearer's motions. For example, the main body 10 may include a sensor, such as a speed sensor, a tilt sensor, an accelerometer, an IMU, and a location detecting device (e.g., a Global Positioning System (GPS)). The main body 10 may include a power supply 16, and the power supply 16 may supply power to various components installed in the main body housing 10a or to the individual drivers 21, 31, and 41 of the walking assistance unit 2. The power supply 16 may be a primary battery or a secondary battery. The primary battery may include at least one of a mercury battery, a manganese battery, an alkaline battery, and a lithium battery. The secondary battery may include a Nickel-Cadmium (Ni—Cd) cell, a Nickel-Hydride (Ni(OH)2) cell, a lead acid battery, a lithium-ion (Li-ion) cell, and a lithium polymer cell.

Figure 25:
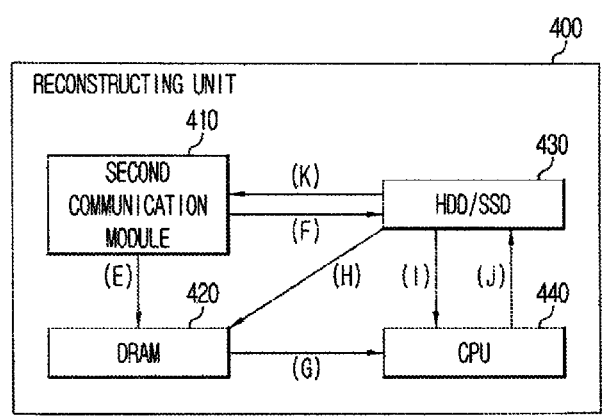
FIG. 25 is a block diagram of a reconstructing unit of a walking management system, according to some example embodiments.

FIG. 25 is a block diagram of a reconstructing unit of a walking management system, according to an embodiment of the present disclosure. In FIG. 25, a server 400 is shown as an example of a reconstructing unit of reconstructing transmission data to acquire a reconstructed signal, however, the reconstructing unit is not limited to the server 400. The reconstructing unit may be one of various units, such as a smart phone or a tablet PC, capable of processing information. Also, the walking assistance robot 1 as described above may be an example of the reconstructing unit.

Referring to FIG. 25, the reconstructing unit 400 may include a second communication module 410, a temporal storage unit (e.g., DRAM) 420, a storage unit (e.g., HDD/SDD) 430, and a Central Processing Unit (CPU) 440.

The second communication module 410 may receive transmission data through a wired/wireless communication network. The transmission data may be transferred to the temporary storage unit 420 to be temporarily stored in the temporary storage unit 420, or the transmission data may be transferred to the storage unit 430 to be non-temporarily stored in the storage unit 430. The transmission data stored in the temporary storage unit 420 or the storage unit 430 may be transferred to the CPU 440 (G and I). In this case, the transmission data stored in the storage unit 430 may be stored in the temporary storage unit 420 (H) and then transferred to the CPU 440 (G).

The CPU 440 may reconstruct the transmission data to acquire a reconstructed signal. The CPU 440 may analyze the transmission data acquired by packetizing signal-analyzed data and reference data to extract the signal-analyzed data and the reference data from the transmission data, decide signal-analyzed data and reference data corresponding to each other from among the extracted signal-analyzed data and the extracted reference data, and then correct the reference data according to the signal-analyzed data, thereby acquiring a reconstructed signal. In this case, the CPU 440 may partition the reference data based on feature points of the signal-analyzed data to acquire a plurality of partitioned reference data, move points of the partitioned reference data, corresponding to the feature points of the signal-analyzed data, according to the feature points of the signal-analyzed data to modify the partitioned reference data, and then combine a plurality of partitioned, modified reference data to thus acquire a reconstructed signal. Also, the CPU 440 may estimate and reconstruct a waveform of signal from the signal-analyzed data based on the reference data, thereby acquiring reconstructed signals corresponding to the walking signals z1, z2, and z3. The reconstructed signals may be transferred to and stored in the storage unit 430 (J). The reconstructed signals may be transferred to the second communication module 420 (K), and then transferred to the walking assistance robot 1 or to another terminal 500 or 600 as necessary.

Hereinafter, a method of converting and reconstructing a signal, according to an embodiment of the present disclosure will be described with reference to FIGS. 26 and 27.

Figure 26:
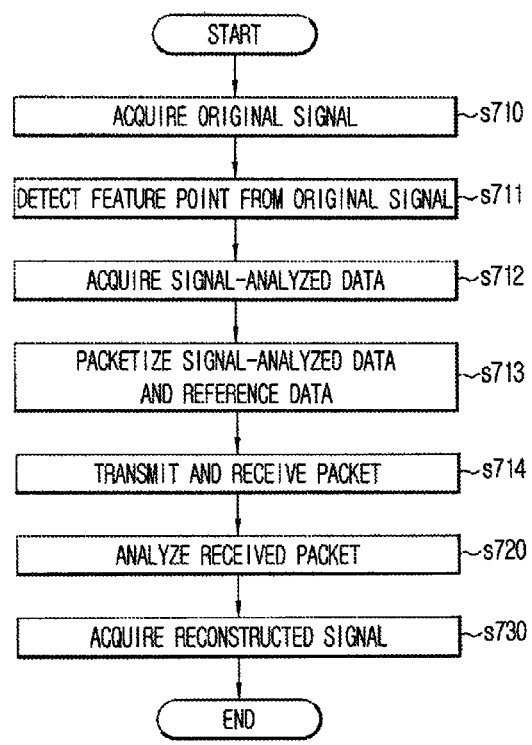
FIG. 26 is a flowchart illustrating a method of converting and reconstructing a signal, according to some example embodiments.

FIG. 26 is a flowchart illustrating a method of converting and reconstructing a signal, according to some example embodiments.

Referring to FIG. 26, the method of converting and reconstructing a signal may include operations S710 to S714 of converting an original signal to store or transmit the original signal, and operations S720 to S730 of acquiring a reconstructed signal corresponding to the original signal based on the converted signal.

In operation S710, the processor 17 may acquire an original signal may be acquired. Herein, the original signal may be a plurality of walking signals output from the individual structure units 20, 30, and 40 of the walking assistance robot 1 (see FIG. 23). The original signal may be normalized as necessary.

In operations S711 and S712, the processor 17 may detect feature points from the acquired original signal or the normalized original signal to acquire signal-analyzed data corresponding to the original signal. The feature points may be points of the original signal or the normalized original signal, which can be features for distinguishing the original signal or the normalized original signal from other signals. The feature points may include at least one of a start point, an end point, a relative maximum point, a relative minimum point, and an inflection point of the original signal or the normalized original signal.

In operation S713, if the signal-analyzed data is acquired, the processor 17 may packetize the signal-analyzed data and reference data corresponding to the signal-analyzed data to acquire a data packet to be transmitted or stored. In this case, a plurality of reference data or a plurality of signal-analyzed data may be included in a data packet. The reference data is data that is referred when a reconstructed signal is generated based on the signal-analyzed data. The reference data may be a waveform of waves.

In operation S714, after the packetization has terminated or when a desired (or, alternatively, a predetermined) time period has elapsed after the packetization has terminated, the processor 17 may transmit the data packet to the reconstructing unit 200 or a storage unit through a wired/wireless communication network. The reconstructing unit 200 or the storage unit may receive the packet, and temporarily or permanently store the received packet.

In operation S720, in order for the reconstructing unit 200 to acquire a reconstructed signal from the received packet, the reconstructing unit 200 may analyze the received packet to extract reference data and signal-analyzed data from the received packet.

In operation S730, the reconstructing unit 200 may reconstruct the original signal using the extracted reference data and the extracted signal-analyzed data.

Figure 27:
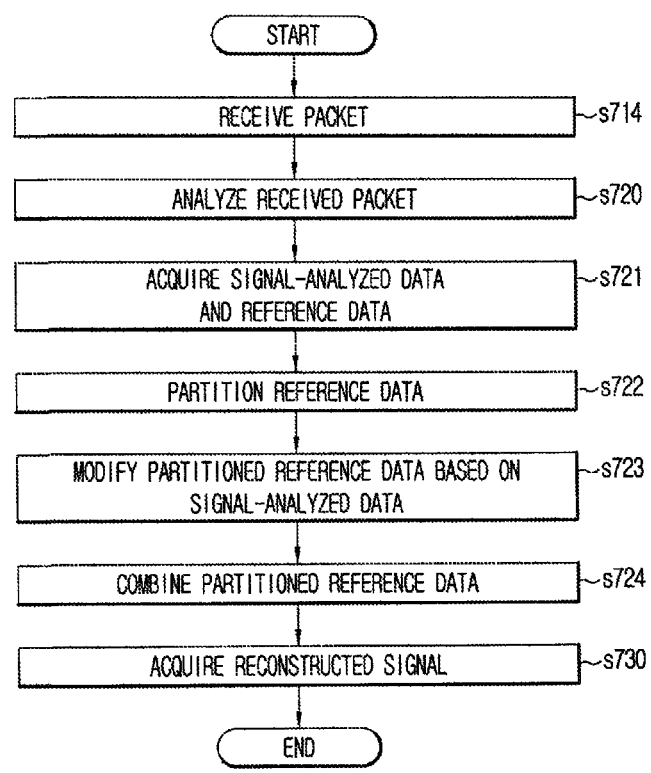
FIG. 27 is a flowchart illustrating a method of acquiring a reconstructed signal, according to some example embodiments.

FIG. 27 is a flowchart illustrating a method of acquiring a reconstructed signal, according to some example embodiments.

As illustrated in FIGS. 26 and 27, and as discussed above, in operations S714 and S720, the reconstructing unit 200 may receive the packet and analyze the received packet.

Further, in operation S721, the reconstruction unit 200 may extract the reference data and the signal-analyzed data from the packet. Then, in operation S722, the reconstructing unit may partition the reference data based on the signal-analyzed data to acquire at least one partitioned reference data.

In operation S723, the reconstructing unit 200 may modify the at least one partitioned reference data based on the signal-analyzed data. The reconstructing unit may move a start point and/or an end point of the reference data in a desired (or, alternatively, a predetermined) direction according to the signal-analyzed data to move the reference data in a desired (or, alternatively, a predetermined) direction, such as an x-axis direction or a y-axis direction, or to extend or reduce the reference data and thus modify the reference data.

Thereafter, in operation S724, the reconstructing unit 200 may connect start points and end points of a plurality of partitioned, modified reference data to combine the plurality of partitioned, modified reference data. In operation S730, the reconstruction unit may acquire a reconstructed signal based on the combined partitioned reference data.

In the above-described embodiments, elements of the wearable robot may be implemented by configuring a processor as a special purpose computer to perform the functions of various 'modules'.

In more detail, the walking assistance robot 1 may include a main body 10 having a processor 17 and a memory therein.

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the processing device as a special purpose computer to perform the operations illustrated in FIGS. 26 and 27, such that the processor 17 converts original walking data into signal analyzed walking data having a smaller size than the original walking data and reconstructs the original walking data using the signal analyzed walking data and reference data. Moreover, the processor 17 may control the movement of the walking assistance robot 1 based on the reconstructed original walking data.

The instructions utilized by the processor 17 may be stored on a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion. The program instructions may be executed by one or more processors.

Although some example embodiments have been shown and described, it would be appreciated by those skilled in the art that changes may be made in these example embodiments without departing from the principles and spirit of the example embodiments, the scope of which is defined in the claims and their equivalents.

What is claimed is:

1. A method of converting and reconstructing a signal, comprising:
    acquiring, via a processor, signal-analyzed data from an original signal generated by at least one sensor, the signal-analyzed data including at least two feature points of the original signal;
    communicating, by the processor, the signal-analyzed data and at least one reference data corresponding to the signal-analyzed data, the at least one reference data being generated based on an average value or an intermediate value of a plurality of different original signals at a time;
    reconstructing, by the processor, the original signal based on the signal-analyzed data and the at least one reference data to generate a reconstructed signal, the reconstructing including,
        detecting, by the processor, at least two points in the reference data corresponding to the at least two feature points,
        partitioning, by the processor, the reference data based on the at least two points in the reference data,
        modifying, by the processor, the partitioned reference data based on the signal-analyzed data such that a distance between two of the at least two points in the modified partitioned reference data is same as a distance between corresponding ones of the at least two feature points in the signal-analyzed data, and
        combining, by the processor, the modified partitioned reference data to generate the reconstructed signal; and
    controlling at least one driver based on the reconstructed signal.

2. The method according to claim 1, wherein the processor is included in a walking assistance robot, the walking assistance robot including the at least one driver, and the original signal includes an operation signal representing an operation of the at least one driver.

3. The method according to claim 1, wherein the at least two feature points includes at least two of a start point, an end point, an inflection point, a point having a relative maximum value, a point having a relative minimum value, a point having a maximum value, and a point having a minimum value of the original signal.

4. The method according to claim 1, wherein the acquiring of the signal-analyzed data from the original signal comprises:
   normalizing the original signal to generate a normalized original signal; and
   extracting the at least two feature points from the normalized original signal.

5. The method according to claim 1, wherein the acquiring of the signal-analyzed data from the original signal further comprises:
   at least one of deciding reference data corresponding to the original signal based on the signal-analyzed data, and generating reference data corresponding to the original signal based on the signal-analyzed data.

6. The method according to claim 1, wherein the communicating comprises:
   storing the signal-analyzed data;
   generating at least one communication packet based on the stored signal-analyzed data and the at least one reference data; and
   communicating the at least one communication packet.

7. The method according to claim 6, wherein the at least one communication packet includes a signal-analyzed data storage area in which the signal-analyzed data is stored, and a reference data storage area in which the at least one reference data is stored.

8. The method according to claim 6, wherein the at least one communication packet includes a plurality of signal-analyzed data storage areas in which a plurality of signal-analyzed data acquired from different original signals are respectively stored, and a plurality of reference data storage areas respectively corresponding to the plurality of signal-analyzed data storage areas, the plurality of reference data storage areas storing reference data corresponding to signal-analyzed data stored in the corresponding signal-analyzed data storage areas.

9. The method according to claim 1, further comprising:
   generating at least one reference data corresponding to the original signal based on the original signal.

10. The method according to claim 1, wherein the communicating comprises:
    transmitting and receiving the signal-analyzed data and the at least one reference data corresponding to the original signal using one or more of a wired communication network, a wireless communication network, and a wired and wireless composite network.

11. A system of converting and reconstructing a signal, comprising:
    a processor and a memory, the memory including machine readable code, that when executed by the processor, configures the processor to,
        acquire signal-analyzed data including at least one feature point acquired from a signal pattern of an original signal generated by at least one sensor
        reconstruct the original signal based on the signal-analyzed data and the at least one reference data to generate a reconstructed signal, the at least one reference data being generated based on an average value or an intermediate value of a plurality of different original signals at a time, the processor configured to reconstruct the original signal by,
            detecting at least two points in the reference data corresponding to the at least two feature points;
            partitioning the reference data based on the at least two points in the reference data;
            modifying the partitioned reference data based on the signal-analyzed data such that a distance between two of the at least two points in the modified partitioned reference data is same as a distance between corresponding ones of the at least two feature points in the signal-analyzed data; and
            combining the modified partitioned reference data to generate the reconstructed signal, and
        controlling at least one driver based on the reconstructed signal.

12. The system according to claim 11, wherein processor is included in a walking assistance robot, the walking assistance robot including the at least one driver, and the original signal includes an operation signal representing an operation of the at least one driver.

13. The system according to claim 11, wherein the processor is included in at least one of a server, a desktop computer, a laptop computer, a smart phone, a cellular phone, a tablet Personal Computer (PC), a Personal Digital Assistant (PDA), and a navigation system.

14. The system according to claim 11, further comprising:
    a user terminal configured to receive the reconstructed signal.

15. A method of converting an original signal, comprising:
    acquiring, by a processor, an original signal generated by at least one sensor;
    acquiring, by the processor, signal-analyzed data from the original signal, the signal-analyzed data including at least two feature points acquired from a signal pattern of the original signal;
    deciding, by the processor, at least one reference data corresponding to the original signal by comparing the at least two feature points with feature points associated with a plurality of reference data stored in a reference data database, the at least one reference data being partitionable based on at least two points in the reference data corresponding to the at least two feature points and modifiable based on the signal-analyzed data such that a distance between two of the at least two points in the modified partitioned reference data is same as a distance between corresponding ones of the at least two feature points in the signal-analyzed data; and
    storing, by the processor, the signal-analyzed data and the at least one reference data corresponding to the original signal in a memory.

16. A signal converting apparatus comprising:
    a transmitter configured to output one or more original signals;
    a memory configured to store at least one reference data corresponding to at least one original signal of the one or more outputted original signals; and
    a processor configured to,
        acquire signal-analyzed data from the original signal, the signal-analyzed data including at least two feature points of the original signal,
        decide the at least one reference data corresponding to the one or more outputted original signals by comparing the at least two feature points with feature points associated with a plurality of reference data stored in a reference data database, the at least one reference data being partitionable based on at least two points in the reference data corresponding to the at least two feature points and modifiable based on the signal-analyzed data such that a distance between two of the at least two points in the modified partitioned reference data is same as a distance between corresponding ones of the at least two feature points in the signal-analyzed data, and store the signal-analyzed data and the at least one reference data in the memory.

17. A method of reconstructing an original signal, comprising:

acquiring, via a processor, signal-analyzed data including at least one feature point extracted from an original signal generated by at least one sensor, and at least one reference data corresponding to the original signal;

detecting, via the processor, at least two points in the reference data corresponding to the at least two feature points;

partitioning, via the processor, the reference data based on the points;

modifying, via the processor, the partitioned reference data based on the signal-analyzed data such that a distance between two of the at least two points in the modified partitioned reference data is same as a distance between corresponding ones of the at least two feature points in the signal-analyzed data; and combining, via the processor, the modified partitioned reference data to generate a reconstructed signal; and controlling, via the processor, at least one driver based on the reconstructed signal.

* * * * *